(12) United States Patent
Bar-Tal et al.

(10) Patent No.: US 9,649,046 B2
(45) Date of Patent: May 16, 2017

(54) LINE OF BLOCK DETECTION

(71) Applicant: BIOSENSE WEBSTER (ISRAEL) LTD., Yokneam (IL)

(72) Inventors: Meir Bar-Tal, Haifa (IL); Richard P. M. Houben, Lanaken (BE); Yaniv Ben Zriham, Binyamina (IL); Roy Urman, Karkur (IL); Shmuel Auerbach, Kerem Maharal (IL)

(73) Assignee: BIOSENSE WEBSTER (ISRAEL) LTD, Yokneam (IL)

( * ) Notice: Subject to any disclaimer, the term of this patent is extended or adjusted under 35 U.S.C. 154(b) by 13 days.

(21) Appl. No.: 14/800,883

(22) Filed: Jul. 16, 2015

(65) Prior Publication Data
US 2016/0045123 A1 Feb. 18, 2016

Related U.S. Application Data

(60) Provisional application No. 62/036,270, filed on Aug. 12, 2014.

(51) Int. Cl.
| | | |
|---|---|---|
| A61B 5/04 | (2006.01) | |
| A61B 5/046 | (2006.01) | |
| A61B 5/042 | (2006.01) | |
| A61B 5/0452 | (2006.01) | |
| A61B 5/0464 | (2006.01) | |

(52) U.S. Cl.
CPC ............ *A61B 5/046* (2013.01); *A61B 5/042* (2013.01); *A61B 5/04011* (2013.01); *A61B 5/04012* (2013.01); *A61B 5/0422* (2013.01); *A61B 5/0452* (2013.01); *A61B 5/0464* (2013.01)

(58) Field of Classification Search
CPC . A61B 5/04011; A61B 5/046; A61B 5/04012; A61B 5/042; A61B 5/0422; A61B 5/0452; A61B 5/0464
See application file for complete search history.

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |

(Continued)

FOREIGN PATENT DOCUMENTS

| | | |
|---|---|---|
| EP | 2901953 A1 | 5/2015 |
| EP | 2982293 A1 | 10/2015 |

OTHER PUBLICATIONS

Evans, Fredrick G. et al: "Automatic Detection of Conduction Block Based on Time-Frequency Analysis of Unipolar Electrograms", IEEE Transactions on Biomedical Engineering, Service Center Piscataway, NJ USA, vol. 46, No. 9 (Sep. 1, 1999) ISSN: 0018-9294.

(Continued)

*Primary Examiner* — Joseph Dietrich
(74) *Attorney, Agent, or Firm* — Louis J. Capezzuto

(57) ABSTRACT

Cardiac catheterization is performed by recording electrograms from a multi-electrode probe at respective locations in the heart, determining slopes and annotations in the electrograms within time windows, establishing relationships among the slopes and annotations of the electrograms, and determining lines of conduction block in the heart from the relationships.

16 Claims, 36 Drawing Sheets

(56) References Cited

U.S. PATENT DOCUMENTS

| 7,536,218 B2 | 5/2009 | Govari et al. |
| 7,756,576 B2 | 7/2010 | Levin |
| 2009/0099563 A1 | 4/2009 | Ciaccio |
| 2012/0101398 A1 | 4/2012 | Ramanathan et al. |
| 2012/0184863 A1 | 7/2012 | Harlev et al. |

OTHER PUBLICATIONS

Auricchio, A. et al.: "Characterization of Left Ventricular Activation in Patients with Heart Failure and Left Bundle-Branch Block", Circulation vol. 109, No. 9, pp. 1133-1139. (Mar. 1, 2004) ISSN: 0009-7322.

Bollacker, Kurt D. et al.: "An Automated Technique for Identification and Analysis of Activation Fronts in a Two-Dimensional Electrogram Array", Computers and Biomedical Research. vol. 27, No. 3 (Jun. 1, 1994) pp. 229-244. ISSN: 0010-4809.

Potse, M.: "Chapter 3 Analysis of Intracardial Electrograms", Integrated Electrocardiographic Mapping. Combined Analysis of Multichannel Endocardial and Body Surface ECG data, (Jan. 1, 2001) URL:http://hdl.handle.net/11245/1.181461 (retrieved Jun. 2, 2016).

European Search Report from EP15180488.7 (Mar. 10, 2016).

Auricchio Characterization of Left Ventricular Activation in Patients With Heart Failure and Left Bundle-Branch Block. Circulation. 2004;109:1133-1139.

U.S. Appl. No. 62/036,270, filed Aug. 12, 2014.
U.S. Appl. No. 14/024,859, filed Sep. 12, 2013.
U.S. Appl. No. 14/574,578, filed Dec. 18, 2014.
U.S. Appl. No. 14/585,828, filed Dec. 30, 2014.

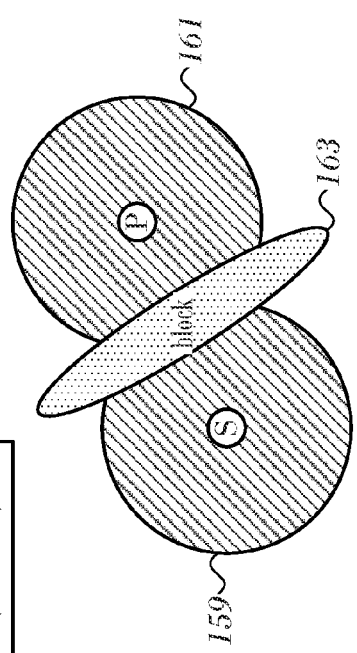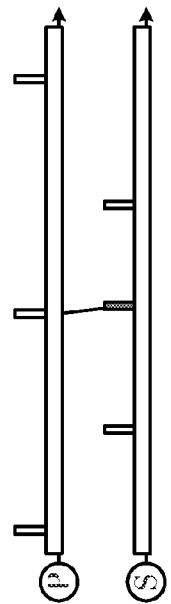
FIG. 10
Coupled Prim/Sec
(non contact)
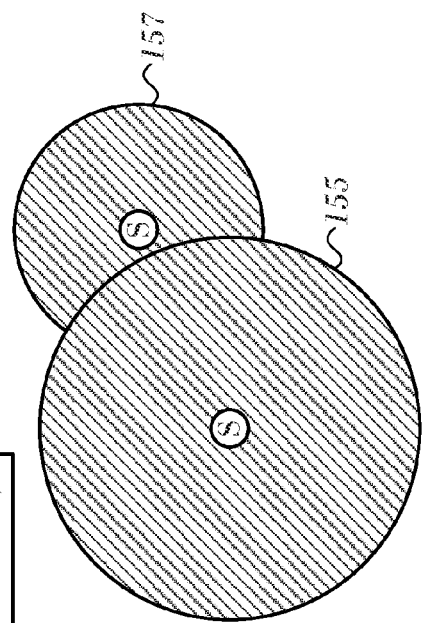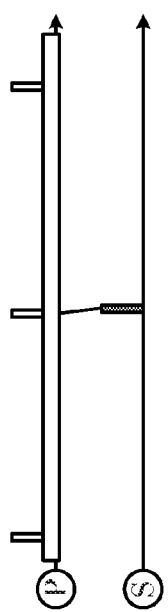
FIG. 11
Coupled Prim/Sec
(contact)

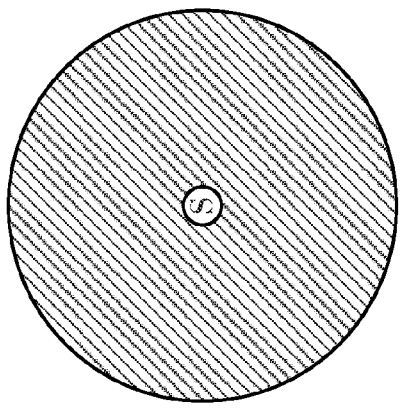
FIG. 13
Uncouped (solitary)
See/See Slopes Planar
(non contact)
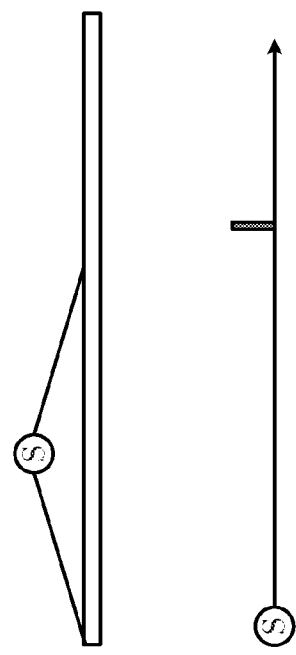
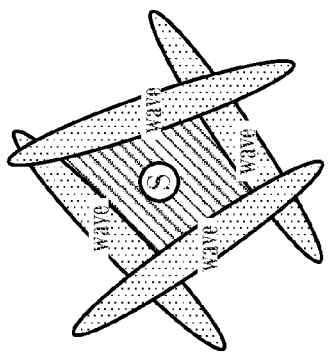
FIG. 12
Uncouped (solitary)
See/See Remote (contact)
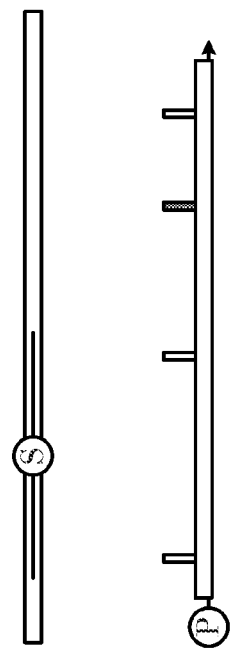

FIG. 14

Uncouped (group)
Sec/Sec Slopes Remote
(all contact)

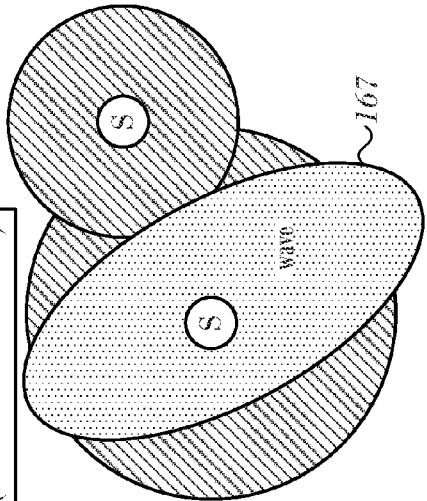

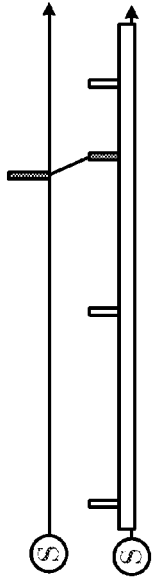

In the case of contact of a set (>1) of recording electrodes related to the coupled secondary slopes (S), but not coupled to a primary slope, a (narrow) wave may have been missed, propagating between these electrode(s).

FIG. 15

Uncouped (group)
Sec/Sec Slopes Planar
(contact/non contact)

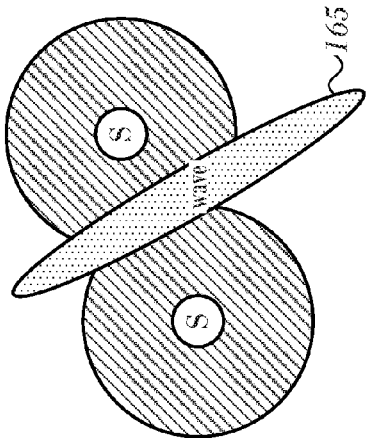

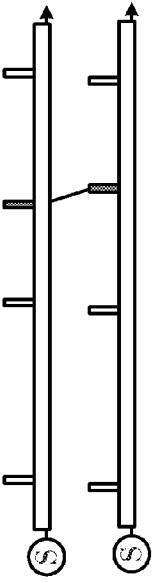

In the case of contact of only one recording electrode related to the coupled secondary slopes (S), but not coupled to a primary slope, a (broader) wave may have been missed, propagating distal from the contact electrode(s).

*FIG. 16*
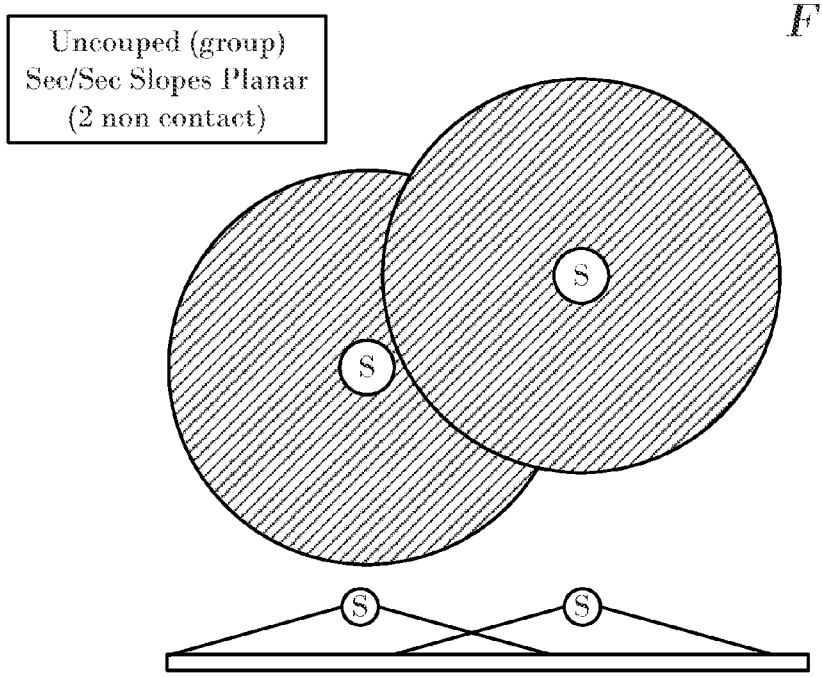
In the case of non contact of the recording electrodes related to the secondary slopes (S), through not coupled to a primary slope, indicates non contact of a larger electrode area, i.e. only P from more distal (time shifted) primary slopes are available.
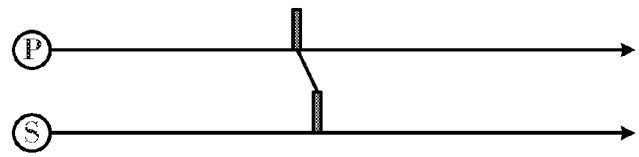
*FIG. 17*
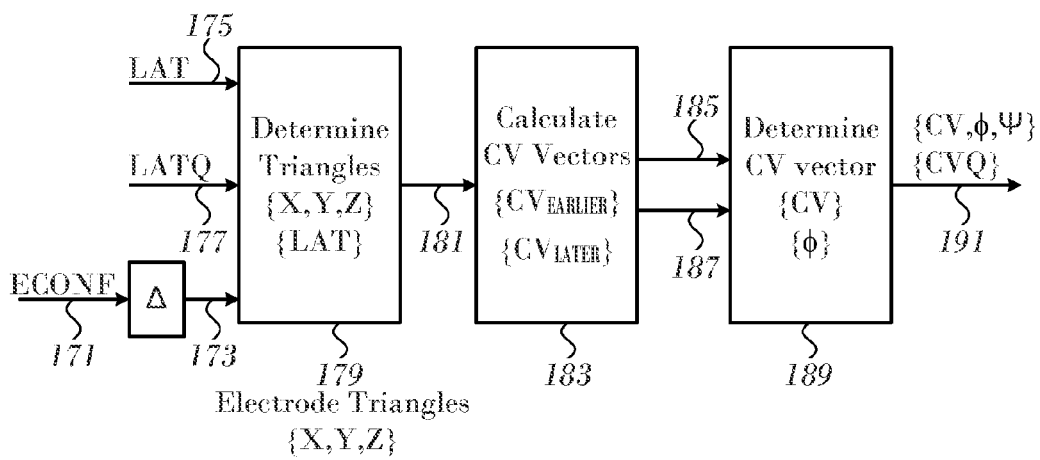

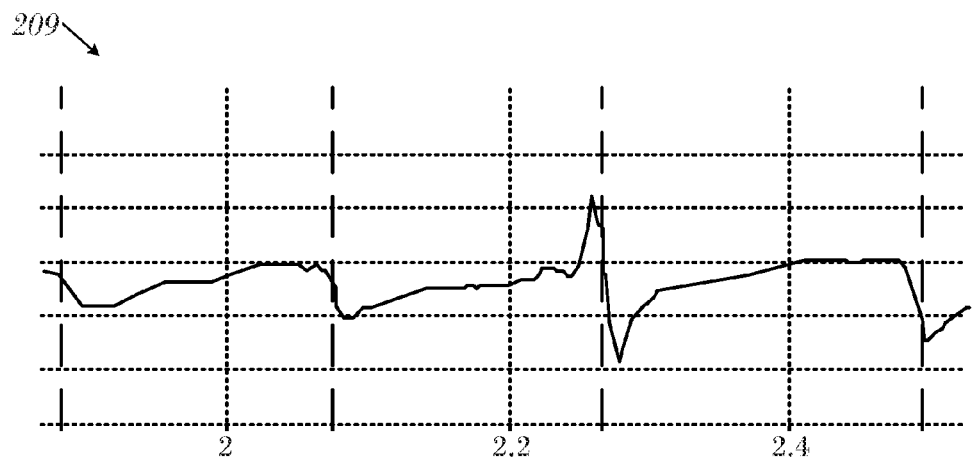
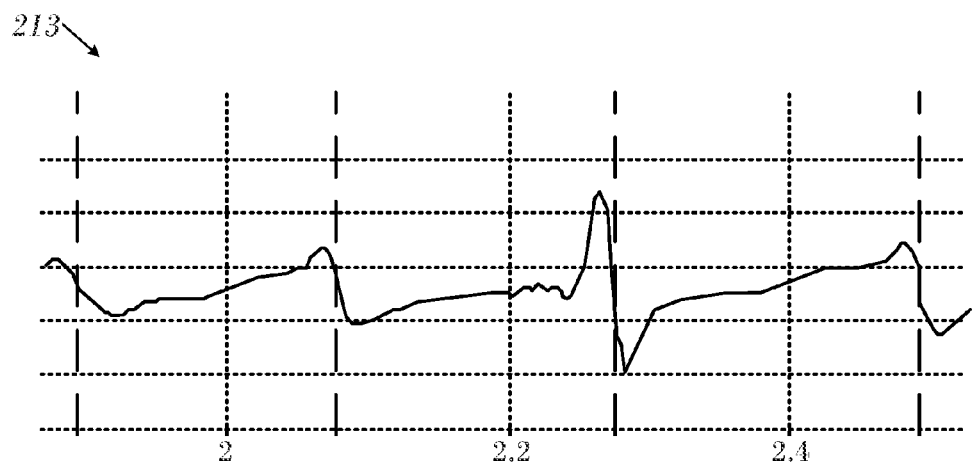
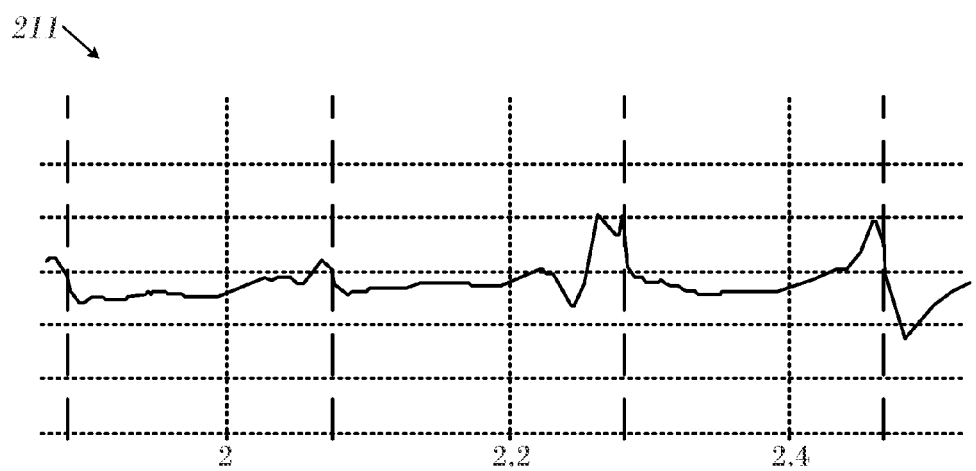
FIG. 20

FIG. 25

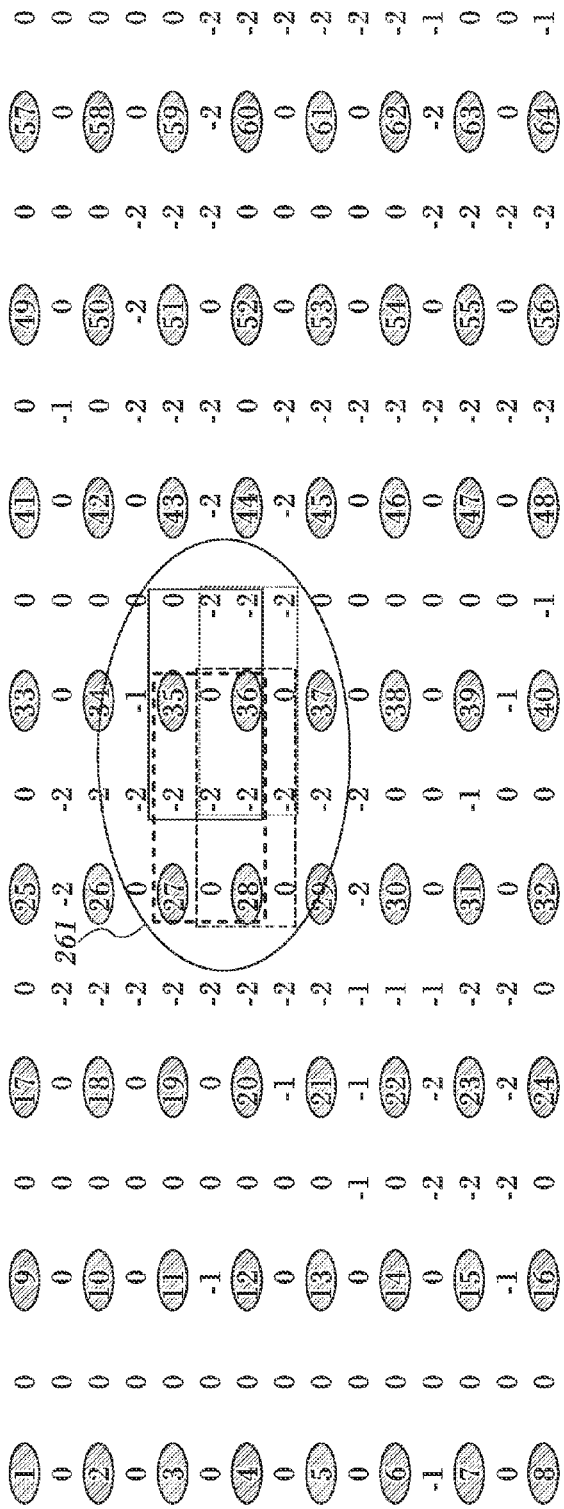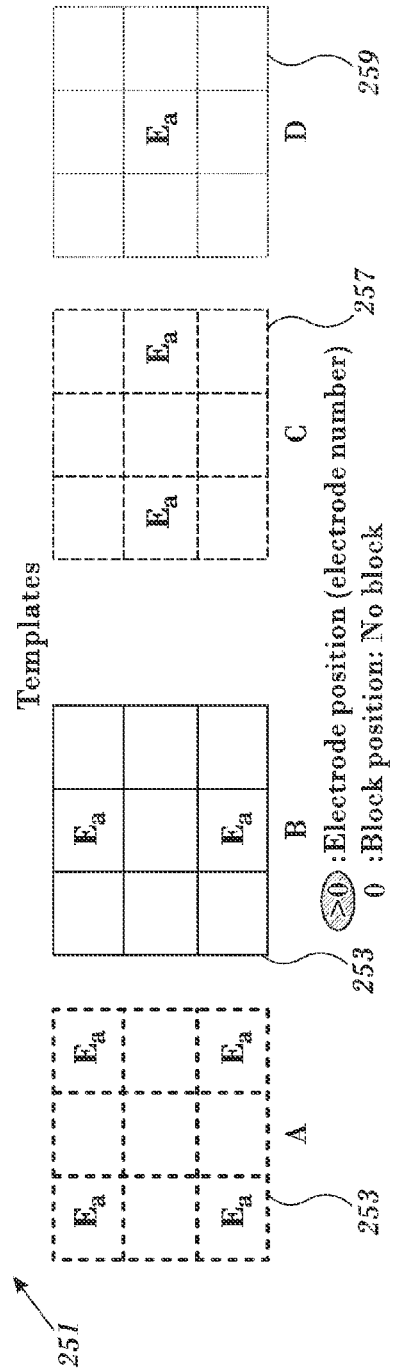
FIG. 27

FIG. 29

WAVE PATTERN: PLANAR PARALLEL

| o100 | o100 | o100 | o100 | o100 | o100 | o100 | o100 |
|------|------|------|------|------|------|------|------|
| o105 | o105 | o105 | o105 | o105 | o105 | o105 | o105 |
| o110 | o110 | o110 | o110 | o110 *331* | o110 | o110 | o110 |
| o115 | o115 | o115 | o115 | o115 | o115 | o115 | o115 |
| o120 | o120 | o120 | o120 | o120 | o120 | o120 | o120 |
| o125 | o125 | o125 | o125 | o125 | o125 | o125 | o125 |
| o130 | o130 | o130 | o130 | o130 | o130 | o130 | o130 |
| o135 | o135 | o135 | o135 | o135 | o135 | o135 | o135 | nrep=50;  Number of waves: 50
trep=150;  Wave repetition time: 150ms
tstart=100;  Start time: wave1=100ms CV=1;  phi=0;  CV=1m/s, phi=0 degrees)
sx=0;  sy=0;  Wave start at (0,0)
nx=8;  ny=8;  8x8 square
dx=5;  dy=5;  Inter electrode distance electrodeStructures=createFlat88;
[t,pos]=generatePlanarWave...
(CV,phi,sx,sy,nx,ny,dx,dy,nrep,trep,tstart,PLOT);

WAVES IDENTIFIED: ACTIVATION MAPS

W1:100-135

| 100 | 100 | 100 | 100 | 100 | 100 | 100 | 100 |
|-----|-----|-----|-----|-----|-----|-----|-----|
| 105 | 105 | 105 | 105 | 105 | 105 | 105 | 105 |
| 110 | 110 | 110 | 110 | 110 | 110 | 110 | 110 |
| 115 | 115 | 115 | 115 | 115 | 115 | 115 | 115 |
| 120 | 120 | 120 | 120 | 120 | 120 | 120 | 120 |
| 125 | 125 | 125 | 125 | 125 | 125 | 125 | 125 |
| 130 | 130 | 130 | 130 | 130 | 130 | 130 | 130 |
| 135 | 135 | 135 | 135 | 135 | 135 | 135 | 135 |

W2:250-285

| 250 | 250 | 250 | 250 | 250 | 250 | 250 | 250 |
|-----|-----|-----|-----|-----|-----|-----|-----|
| 255 | 255 | 255 | 255 | 255 | 255 | 255 | 255 |
| 260 | 260 | 260 | 260 | 260 | 260 | 260 | 260 |
| 265 | 265 | 265 | 265 | 265 | 265 | 265 | 265 |
| 270 | 270 | 270 | 270 | 270 | 270 | 270 | 270 |
| 275 | 275 | 275 | 275 | 275 | 275 | 275 | 275 |
| 280 | 280 | 280 | 280 | 280 | 280 | 280 | 280 |
| 285 | 285 | 285 | 285 | 285 | 285 | 285 | 285 |

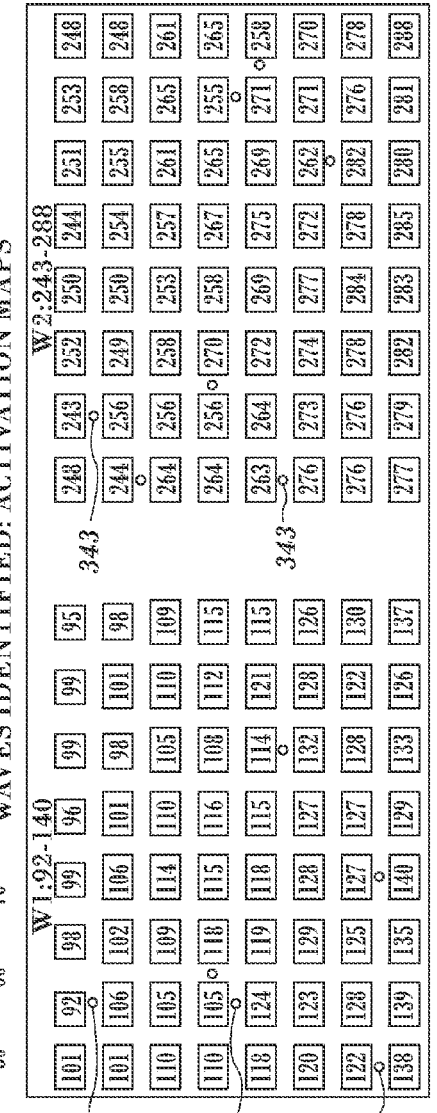
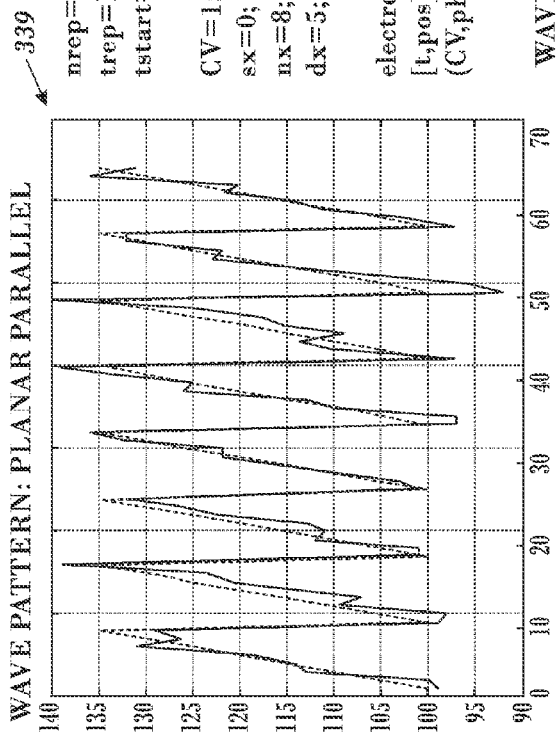
FIG. 40

WAVE PATTERN: PLANAR DISSOCIATED

| | | | | | | | |
|---|---|---|---|---|---|---|---|
| o150.00 | o150.00 | o150.00 | o250.00 | o250.00 | o250.00 | o250.00 | o250.00 |
| o155.00 | o155.00 | o155.00 | o155.00 | o255.00 | o255.00 | o255.00 | o255.00 |
| o160.00 | o160.00 | o160.00 | o160.00 | o260.00 | o260.00 | o260.00 | o260.00 |
| o165.00 | o165.00 | o165.00 | o165.00 | o265.00 | o265.00 | o265.00 | o265.00 |
| o170.00 | o170.00 | o170.00 | o170.00 | o270.00 | o270.00 | o270.00 | o270.00 |
| o175.00 | o175.00 | o175.00 | o175.00 | o275.00 | o275.00 | o275.00 | o275.00 |
| o180.00 | o180.00 | o180.00 | o180.00 | o280.00 | o280.00 | o280.00 | o280.00 |
| o185.00 | o185.00 | o185.00 | o185.00 | o285.00 | o285.00 | o285.00 | o285.00 |

345, 347

Timing
nrep=50;
trep=150;
Mapping array
nx=8;  ny=8;
dx=5;  dy=5;
Per wave
tstart=150,250;
CV=1,1;
Phi=0,0;
sx=0,0; sy=0,0;

Number of waves: 50
Wave repetition time: 150ms

8x8 square
Inter electrode distance

Start time: wave1 = 150ms, wave2 = 250 ms
CV: wave1 = 1m/s, wave2 = 1m/s
Phi: wave1 = 0°, wave2 = 0°
Start: wave1 = (0,0), wave2 = (0,0)

WAVES IDENTIFIED: ITERATION PROGRESSION

WAVE PATTERN: PLANAR U-TURN

| 100 | 100 | 100 | 100 | 170 | 170 | 170 | 170 |
|-----|-----|-----|-----|-----|-----|-----|-----|
| 105 | 105 | 105 | 105 | 165 | 165 | 165 | 165 |
| 110 | 110 | 110 | 110 | 160 | 160 | 160 | 160 |
| 115 | 115 | 115 | 115 | 155 | 155 | 155 | 155 |
| 120 | 120 | 120 | 120 | 150 | 150 | 150 | 150 |
| 125 | 125 | 125 | 125 | 145 | 145 | 145 | 145 |
| 130 | 130 | 130 | 130 | 140 | 140 | 140 | 140 |
| 135 | 135 | 135 | 135 | 135 | 135 | 135 | 135 |

Timing
nrep=50;
trep=150;

Mapping array
nx=8;   ny=8;
dx=5;   dy=5;

Per wave
tstart=100,135;
CV=1,1;
Phi=0,0;
sx=0,0; sy=0,7;

Number of waves: 50
Wave repetition time: 150ms

8x8 square
Inter electrode distance

Start time: wave1 = 100ms, wave2 = 135 ms
CV: wave1 = 1m/s, wave2 = 1m/s
Phi: wave1 = 0°, wave2 = 180°
Start: wave1 = (0,0), wave2 = (0,7)

WAVES IDENTIFIED: ITERATION PROGRESSION

W1: 100-170         W2: 250-320

LINE OF BLOCK DETECTION

CROSS-REFERENCE TO RELATED APPLICATIONS

This Application claims the benefit of U.S. Provisional Application No. 62/036,270, filed 12 Aug. 2014, which is herein incorporated by reference.

BACKGROUND OF THE INVENTION

Field of the Invention

This invention relates to evaluation of a medical condition by analysis of electromagnetic signals. More particularly, this invention relates to improvements in detecting and measuring certain aspects of the electrocardio-graphic cycle.

Description of the Related Art

The meanings of certain acronyms and abbreviations used herein are given in Table 1.

TABLE 1

Acronyms and Abbreviations

| | |
|---|---|
| 3-D | 3-dimensional |
| LV | Left Ventricle |
| LBBB | Left Bundle Branch Block |
| ECG | Electrocardiogram |
| MRI | Magnetic Resonance Imaging |
| LAT | Local Activation Time |
| IC-ECG | Intracardiac ECG |
| WOI | Window of Interest |
| FF | Far Field |
| NF | Near Field |
| IC-EGM | Intracardiac Electrograms |
| EGM | Electrogram |

Three-dimensional (3-D) images of internal organs are useful in many catheter-based diagnostic and therapeutic applications, and real-time imaging is widely used during surgical procedures.

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, also referred to herein as a conduction velocity vector, which is normal to an isoelectric activation front, both of which may be derived from a map of activation time. The rate of propagation of the activation front through any point in the endocardium may be represented as a conduction velocity vector.

Localized defects in the heart's conduction of activation signals may be identified by observing phenomena such as multiple activation fronts, abnormal concentrations of activation vectors, or changes in the velocity vector or deviation of the vector from normal values. Examples of such defects include reentrant areas, which may be associated with signal patterns known as complex fractionated electrograms. Once a defect is located by such mapping, it may be ablated (if it is functioning abnormally) or otherwise treated to restore the normal function of the heart insofar as is possible.

The document *Characterization of Left Ventricular Activation in Patients With Heart Failure and Left Bundle-Branch Block*, Auricchio et al., Circulation. 2004; 109:1133-1139 describes LV activation sequences in patients with heart failure and LBBB QRS morphology with simultaneous application of 3-D contact and noncontact mapping during intrinsic rhythm and asynchronous pacing. A "U-shaped" activation wave front was present in most of the patients because of a line of block that was located anteriorly, laterally, or inferiorly. Functional behavior of the line of block was demonstrated by a change in its location during asynchronous ventricular pacing at different sites and cycle length.

SUMMARY OF THE INVENTION

Mapping the activation front and conduction fields aids the physician in identifying and diagnosing abnormalities, such as ventricular and atrial tachycardia and ventricular and atrial fibrillation, which result from areas of impaired electrical propagation in the heart tissue.

For example, commonly assigned copending application Ser. No. 14/024,859, entitled Method for Mapping Ventricular/Atrial Premature Beats During Sinus Rhythm, which is herein incorporated by reference, discloses using a mapping electrode of a probe to associate a local activation time with a region of interest in the heart when a cardiac arrhythmia is inconstantly present.

There is provided according to embodiments of the invention a method, which is carried out by inserting a multi-electrode probe into a heart of a living subject, recording electrograms from the electrodes at respective locations in the heart, determining slopes and annotations in the electrograms within time windows, establishing relationships among the slopes and annotations of the electrograms, and determining lines of conduction block in the heart from the relationships.

A further aspect of the method includes generating an electroanatomic map of the lines of conduction block.

In yet another aspect of the method determining slopes and annotations includes determining bipolar windows in the electrograms, annotating local activation times within the bipolar windows, determining from readings of a set of electrodes that a block point exists in a region of the set of electrodes, repositioning the local activation times responsively to the block point, and determining revised windows that include respective local activation times.

According to still another aspect of the method, establishing relationships among the slopes and annotations includes identifying primary slopes and secondary slopes in the electrograms, determining whether the electrodes are in contact with the heart, and determining whether the primary slopes and the secondary slopes are coupled to one another.

An additional aspect of the method includes identifying a propagation wave responsively to determining whether the primary slopes and the secondary slopes are coupled to one another and to determining whether the electrodes are in contact with the heart.

Another aspect of the method includes computing conduction velocity vectors at the electrodes from the electrograms, making a determination that an activation at a first electrode is dissociated from an activation at a second electrode, and concluding responsively to the determination that a conduction block exists between the first electrode and the second electrode.

Yet an additional aspect of the method includes segmenting the electrograms into frames at respective times, wherein the frames are respective assignments of individual readings of a mesh of electrode readings to a matrix of values.

The frames may comprise vacant positions that are unassigned to readings of the electrodes. An aspect of the method includes reassigning readings of electrodes that are identified with an inter-wave block to the vacant positions.

Still another aspect of the method includes generating electroanatomic maps of the heart from the frames.

There is further provided according to embodiments of the invention an apparatus, including a multi-electrode probe adapted for insertion into a heart of a living subject, and a processor, which is configured to receive an electrical signal from the electrodes and configured for recording electrograms from the electrodes at respective locations in the heart, determining slopes and annotations in the electrograms within time windows, establishing relationships among the slopes and annotations from different ones of the electrograms, and determining from the relationships lines of conduction block in the heart.

The apparatus may include a display, wherein the processor is further configured for generating an electroanatomic map of the lines of conduction block on the display.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 10 is a diagram illustrating detailed relations between coupled primary and secondary slopes detected by electrodes, in accordance with an embodiment of the invention;

FIG. 11 is a diagram illustrating detailed relations between coupled primary and secondary slopes detected by electrodes, in accordance with an embodiment of the invention;

FIG. 12 is a diagram illustrating detailed relations between coupled primary and secondary slopes detected by electrodes, in accordance with an embodiment of the invention;

FIG. 13 is a diagram illustrating detailed relations between coupled primary and secondary slopes detected by electrodes, in accordance with an embodiment of the invention;

FIG. 14 is a diagram illustrating detailed relations between coupled primary and secondary slopes detected by electrodes, in accordance with an embodiment of the invention;

FIG. 15 is a diagram illustrating detailed relations between coupled primary and secondary slopes detected by electrodes, in accordance with an embodiment of the invention;

FIG. 16 is a diagram illustrating detailed relations between coupled primary and secondary slopes detected by electrodes, in accordance with an embodiment of the invention;

FIG. 17 is a data flow chart illustrating the determination of conduction velocity vectors in accordance with an embodiment of the invention;

FIG. 20 is a representative series of three electrograms from electrodes defining a triangle in the grid of FIG. 19 in accordance with an embodiment of the invention;

FIG. 25 is an exemplary frame segmentation map produced by an embodiment of the invention;

FIG. 27 shows an 8×8 electrode block/line matrix that is processed in accordance with an embodiment of the invention;

FIG. 29 shows a block-line matrix that has been subjected to template matching in accordance with an embodiment of the invention.

FIG. 39 is a composite diagram showing a conduction velocity vector of FIG. 38 superimposed on a grid of electrodes and activation maps in accordance with an embodiment of the invention;

FIG. 40 is a composite diagram including a graph illustrating LAT jitter added to a conduction velocity vector of FIG. 38 in accordance with an embodiment of the invention;

FIG. 41 is a composite diagram showing a simulated planar dissociated wave pattern in accordance with an embodiment of the invention;

FIG. 42 is a composite diagram showing activation maps of the planar dissociated wave pattern of FIG. 41 in accordance with an embodiment of the invention FIG. 44 is a composite diagram showing a simulated planar reversal (u-turn) pattern in accordance with an embodiment of the invention.

DETAILED DESCRIPTION OF THE INVENTION

Figure 1:
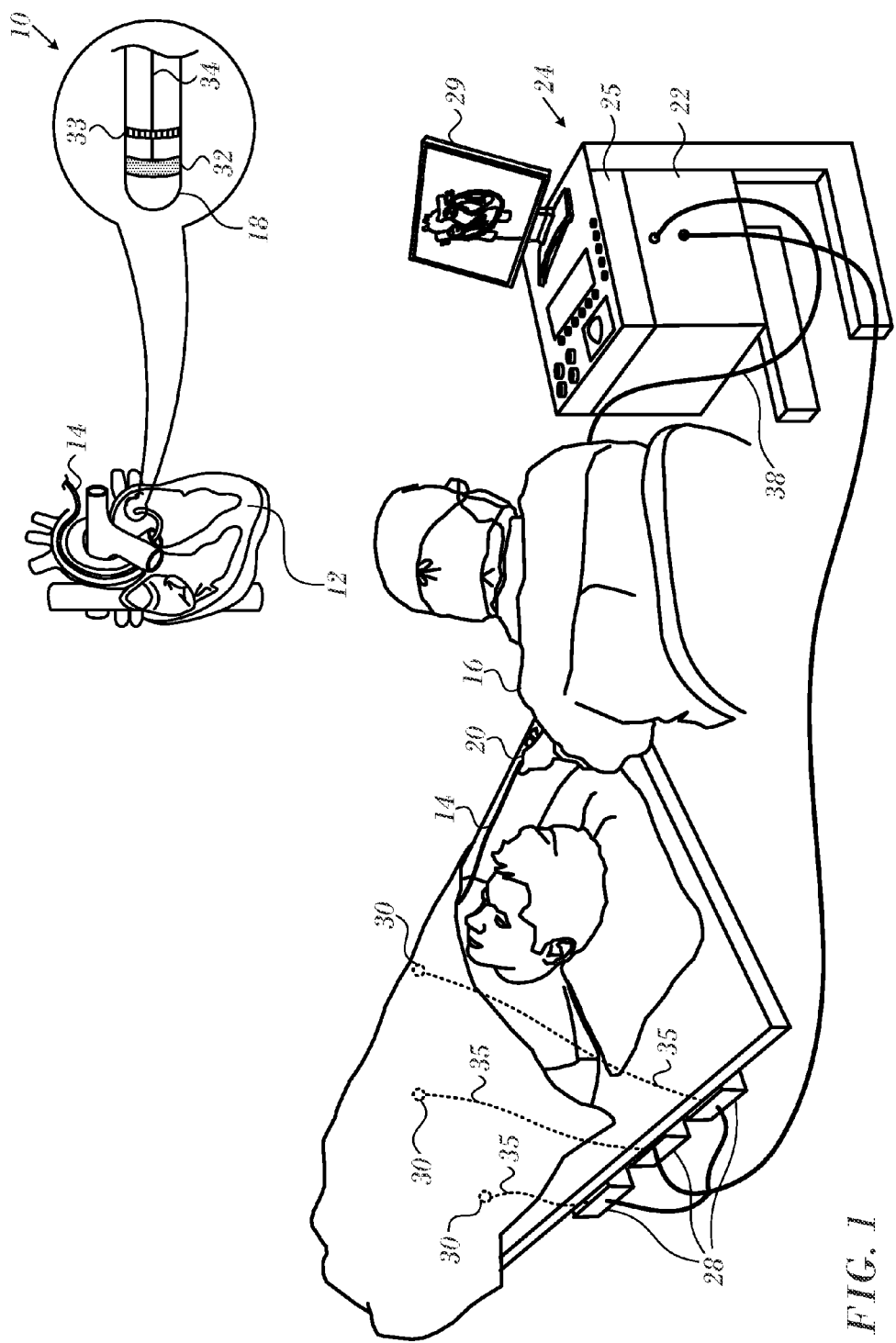
FIG. 1 is a pictorial illustration of a system for evaluating electrical activity in a heart of a living subject in accordance with an embodiment of the invention.

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

DEFINITIONS

"Annotations" or "annotation points" refer to points or candidates on an electrogram that are considered to denote events of interest. In this disclosure the events are typically onset (local activation time) of the propagation of an electrical wave as sensed by the electrode.

"Activity" in an electrogram is used herein to denote a distinct region of bursty or undulating changes in an electrogram signal. Such a region may be recognized as being outstanding between regions of baseline signals. In this disclosure "activity" more often refers to a manifestation on an electrogram of one or more electrical propagation waves through the heart.

A "wave" refers to continuous electrical propagation within a mapped area of the heart.

A "line of block" refers to an impediment or block of electrical propagation in the heart. Such lines may demarcate waves. Waves may themselves contain lines of block, known as "intrawave blocks".

A "primary slope" of an electrogram is a slope related to a local activation time of an activation wave passing under the electrode A "secondary slope" is a slope related to a wave not passing under the electrode, i.e., from a distal activation wave, such as far-field activity.

A slope is "coupled" to another slope when both the slope and the other slope consistently occur within a defined time window A "wavelet" is an expansion of a fixed function by dilation. A wavelet transformation determines the frequency content of a signal as a function of time by using various dilated copies of a mother wavelet.

A "block point" is a point, having a conduction velocity of less than a user-defined value, typically 0.2 m/s. Additionally or alternatively, a block point is a point located between two electrodes wherein an activation wave departing the first electrode arrives at the second electrode to find that the second electrode was previously activated within a user-defined time interval, e.g., 100 ms, immediately prior to the arrival, and after the beginning of the refractory period of the second electrode. For example, consider an electrode that measures activation of the underlying tissue at t=T0 by a wave with a velocity CV. Suppose further a second electrode at a distance D. The tissue under the second electrode was activated starting a refractory period R at T=T1. We now can determine that the time the current wave would activate the tissue under the second electrode is D/CV. If (T+D/CV)<(T1+R), then the tissue is still in its refractory period and therefore blocks activation.

A "line of block" or "block line" is a collection of block points.

A "detour point" refers to a point where there is a change in direction of a wave, e.g., a U-turn.

A "frame" is an assignment of individual readings of a mesh of electrode readings to a matrix of values.

Conduction block lines and conduction block points are often referred to herein for convenience as "block lines", "lines of block" or "block points.

System Overview

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892, 091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally applied reference patch attacked to the exterior of the subject's body, or on an internally placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

Mapping of Atrial Fibrillation Activation

Atrial fibrillation is characterized by a complex pattern of propagation, without periodic or repetitive patterns. There may be multiple lines of block, separating various forms of dissociated waves. Attempts to map atrial activation times to an atrial electrode mesh result in measurement errors. Spatial resolution based on electrode readings from a mapping catheter is inadequate for evaluating complex atrial fibrillation activation patterns.

The procedures described herein detects atrial waves delineated by lines of block within a context of frames, i.e., segmentation, described below.

Figure 2:
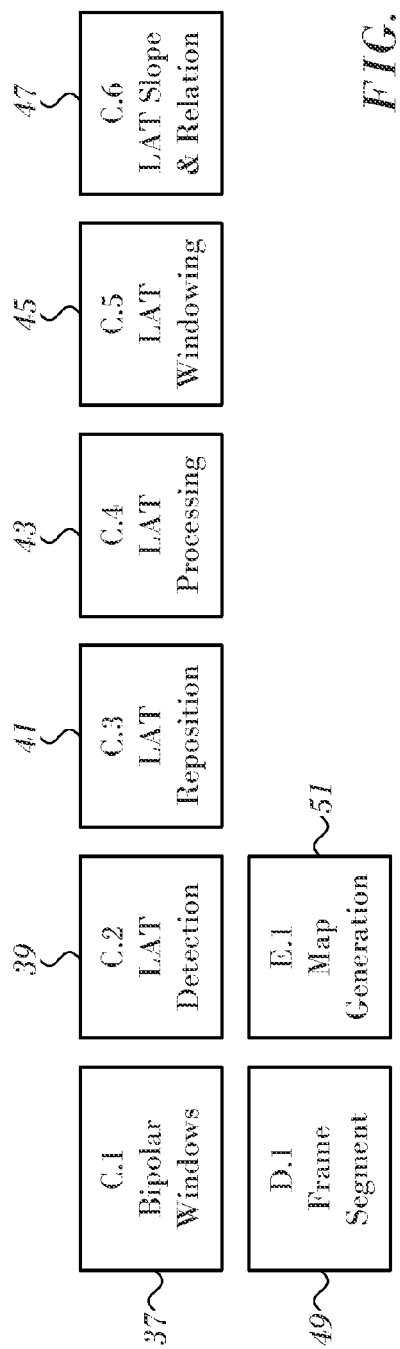
FIG. 2 is a block diagram of an approach to evaluating atrial fibrillation activation in accordance with an embodiment of the invention.

These procedures may be implemented using a unified Matlab® framework. Application of the principles of the invention described in the following embodiments enable spatio-temporal structures in atrial fibrillation to be characterized and identified as potential ablation targets. Reference is now made to FIG. 2, which is a block diagram of a general approach to evaluating atrial fibrillation activation in accordance with an embodiment of the invention. A process leading to map generation includes identifying bipolar windows in block 37 from preprocessed electrograms in which ventricular far-field potentials have been removed. Removal of far-field effects can be accomplished using the teachings of co-pending application Ser. No. 14/574,578, entitled Ventricular Far Field Reduction, which is herein incorporated by reference. Further steps in the process include LAT detection in block 39, LAT repositioning in block 41, LAT processing in block 43, LAT windowing in block 45, LAT slope and relation detection in block 47, frame segmentation in block 49, and map and matrix generation in block 51.

Identification of lines of blocks use a process of wave mapping after identifying annotations in intracardiac electrograms. These annotations can be from wavelets, which can be computed using the teachings of commonly assigned, co-pending application Ser. No. 14/585,828, entitled Double Bipolar Configuration for Atrial Fibrillation Annotation, which is herein incorporated by reference.

(1) Using the annotations waves are identified by line of block detection in a process of region growing, which is explained below.

(2) Block points are filtered and processed, which may involve revision of annotations.

LAT detection and processing occurs in blocks 37, 39, 41, 43, 45 as taught in the above-noted application Ser. No. 14/585,828.

While performing electro-anatomical mapping of the heart detection of a line of block (Both anatomical and functional) can influence the accuracy of the map. With current 3-D maps, color is interpolated between any two points without taking into account lines of blocks. Without identification of a line of block, color on the map can be interpolated over a non-conducting area and can thus distort the map.

Figure 3:
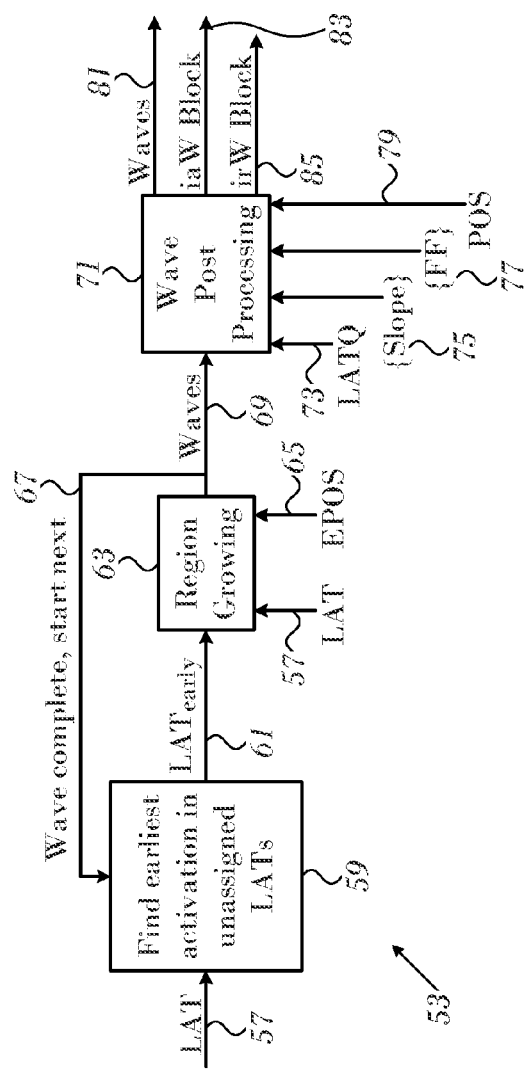
FIG. 3 shows data flow diagrams illustrating wave mapping and line of block detection, in accordance with an embodiment of the invention.

In one embodiment detection of a line of block using a multi-electrode mapping catheter is based on evaluating the LAT of each electrode, the distance between electrodes, the direction of propagation and the physiological probability of conduction in these areas. The strategy employed comprises:

1. Obtain annotations from unipolar electrode wavelets
 2. Prepare a mapping array structured by electrodes, e.g., 3×3 squares of electrodes.
 3. For each mapping array determine LAT time windows, slope, swing amplitude and swing time.
 4. Evaluate LAT quality of the wavelets. Obtain conduction velocity vectors ($CV_{vector}$);
 5. Obtain far-field information (primary and secondary slopes).
 6. For each electrode evaluate intracardiac ECG (IC-ECG) quality at a 1 sec window resolution Reference is now made to FIG. 3, which comprise data flow diagrams 53, 55 illustrating wave mapping and line of block detection, in accordance with an embodiment of the invention. In data flow diagram 53 a series of LAT annotations from multiple electrodes, represented as signal 57, form an input to block 59, which determines the earliest of the LAT annotations. The earliest annotation is output as signal 61 and accepted in block 63, in which a process of region growing is performed. Region growing is explained in further detail below in the discussion of FIG. 22. The earliest annotation forms an element of a wave in a mapping array. The location (EPOS) of a current electrode, corresponding to the electrode that produced signal 61, and the LAT signal 57 are input as signal 65 A feedback signal 67 is returned to block 59 when a wave has been characterized in the block 63. Upon receipt of feedback signal 67, block 59 processes the next received LAT annotation.

The waves defined by block 63 are transmitted as input signal 69 to block 71, which performs wave post processing. Other inputs to block 71 concern the quality of the waves: quality evaluation signal 73, LAT slope signal 75, far field slope signal 77 and position signal 79. The outputs of block 71 are wave signal 81, intrawave (iaW) block signal 83 and interwave (irW) block signal 85. Post processing is explained in further detail below.

Figure 4:
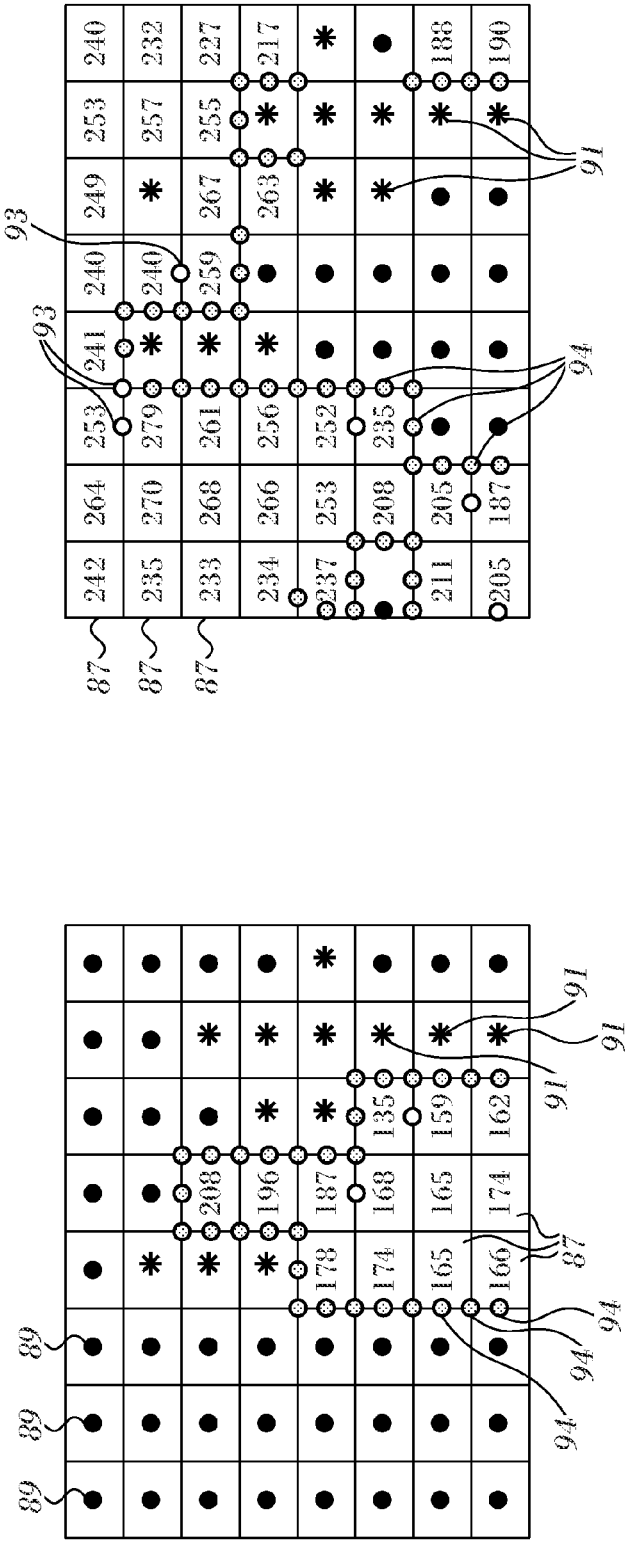
FIG. 4 is an exemplary diagram illustrating mapping of lines of block during atrial fibrillation, in accordance with an embodiment of the invention.

Reference is now made to FIG. 4, which is an exemplary diagram illustrating mapping of lines of block during atrial fibrillation, in accordance with an embodiment of the invention. Local activation times are indicated in squares 87. Electrode positions 89, some obscured by the squares 87, form a grid. Low quality electrode signals are indicated by asterisks 91. These signals are not reliable for LAT determination. Block points 93 have local activation times that lie outside a time window of interest. Lines of block are indicated by a collection of block points 94.

LAT Slope Relation

LAT Slope Relations are evaluated in block 47 (FIG. 2). Conventionally in atrial fibrillation, detection of LATs from contact electrodes by themselves results in poor spatial resolution. According to embodiments of the invention, more information can be extracted from the electrodes by (1) discriminating between electrode contact and non-contact; (2) discriminating between primary slopes (activations at the point of contact) and secondary slopes (caused by remote effects); and (3) consideration of time relations between an electrode and its neighboring electrodes. All of these factors are evaluated in combination. In particular the added information provided by consideration of slope relations compensates for spatial under-sampling by individual and enables accurate projection of activation times in a catheter electrode or anatomical mesh. The algorithm is as follows:

(1) Detect all slopes in all electrodes.
 (2) Discriminate primary (related to LAT) from secondary slopes.
 (3) Determine contact status for all electrodes over time. A contact electrode typically has an adequate number of primary slopes, which are repeated over time. The minimum number of primary slopes is patient-dependent, according to the complexity of the atrial fibrillation pattern being analyzed. A level of 50% primary slopes is typical.
 (4) Relate secondary slopes to primary slope.
 (5) Find coupled secondary slopes in neighboring electrodes, i.e., aligned points of max −dv/dt within overlapping primary and secondary slope windows. When neighboring electrodes are in contact with the heart wall, coupled secondary slopes may result from dissociated waves. When they are not in contact then coupled secondary slopes result from a far field view of the same wave.
 (6) A set of unrelated secondary slopes remains after performing the above steps. These slopes may result from activations occurring between electrodes. Identification of such slopes is useful for mapping.

Figure 5:
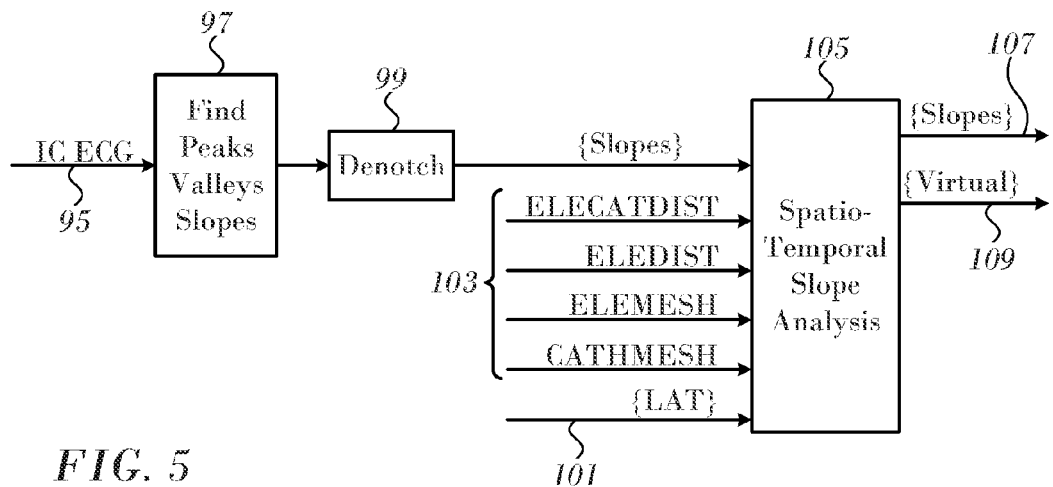
FIG. 5 is a schematic flow diagram illustrating determination of LAT-slope relationships in accordance with an embodiment of the invention.

Reference is now made to FIG. 5, which is a schematic flow diagram illustrating aspects of the determination of LAT-slope relationships, in accordance with an embodiment of the invention. An intracardiac electrogram signal 95 is input to block 97, and its maxima, minima and slopes determined. It is common in atrial fibrillation for interruptions (notches) to occur. Denotching occurs in block 99. The output of block 99, a LAT signal 101 of the IC-ECG and Matlab inputs 103 are input to block 105, where spatiotemporal slope analysis occurs. The outputs are slopes signal 107 and a virtual LAT signal 109. Virtual LATs are derived from detection of a secondary slope that could not be coupled to primary slopes. In other words, none of the electrodes recorded an activation corresponding to the secondary slope. When a wave propagating between two electrodes produces a secondary slope, but fails to produce a primary slope, the secondary slope is designated as a virtual LAT.

Figure 6:
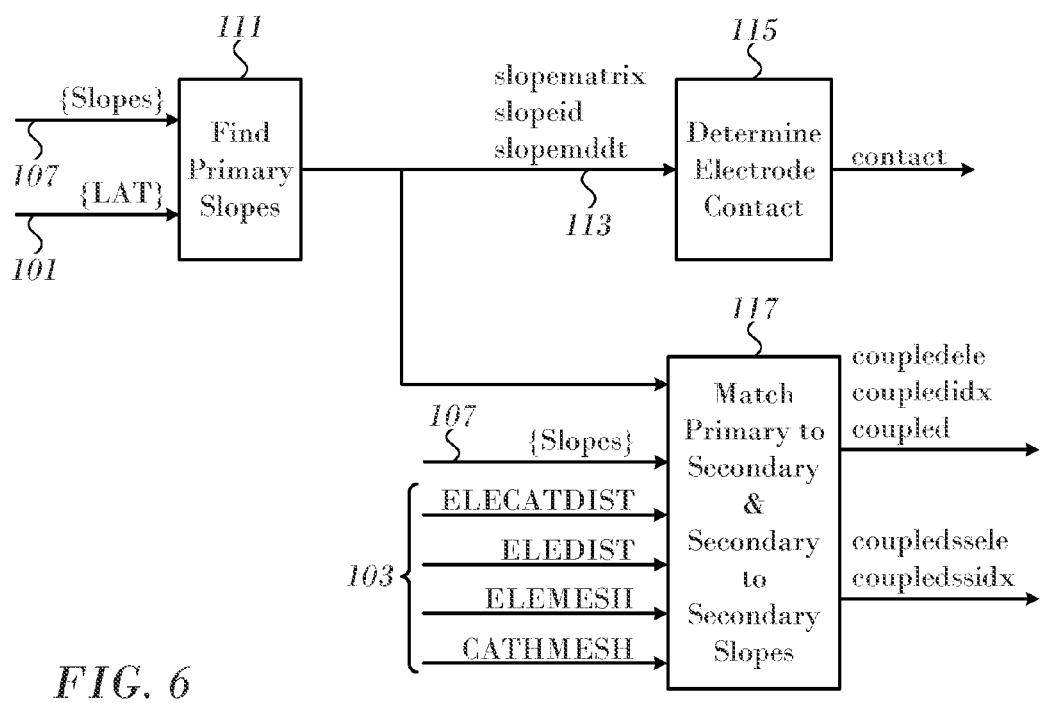
FIG. 6 is a schematic flow diagram illustrating additional aspects of the determination of LAT-slope relationships in accordance with an embodiment of the invention.

Reference is now made to FIG. 6, which is a schematic flow diagram illustrating additional aspects of the determination of LAT-slope relationships in accordance with an embodiment of the invention. The slopes signal 107 and LAT signal 101 are input to block 111, where primary slopes are determined. The output signal 113 includes a slope matrix that is used to determine electrode contact in block 115. The output signal 113, slopes signal 107 and Matlab inputs 103 (ELECADIST, ELEDIST, ELEMESH, CATHMESH) are fed to block 117, where matching of primary and secondary slopes, and matching of secondary slopes with other secondary slopes occur. The inputs ELEMESH and CATHMESH are structured compound variables describing the electrode and catheter mesh geometry respectively. They are implemented as fields of a structure in Matlab. In this application, a mesh is an arranged set of connected nodes and triangles. Each node is a vertex of a triangle. Triangles are coupled by vertices to other triangles making up the mesh. Each mesh contains the number and location (x,y,z) of the nodes. For each triangle, the three vertex nodes are described.

In the electrode mesh ELEMESH, the number of vertices is equal to the number of electrodes on the mapping catheter. In the case of 64 electrodes, there are 64 mesh vertices and 112 triangles. The catheter mesh CATHMESH is an interpolation of the electrode mesh. In this way a smoother surface described by the mesh is obtained by providing more (interpolated) vertices and consequently more triangles. ELEDIST and ELECATDIST and are matrices that contain the distances between each vertex and any other vertex in the electrode and catheter meshes, respectively.

Signals containing information of coupled signals are output from block 117. Relations between primary and secondary slopes are interpreted according to the contact or non-contact status of the electrodes, as explained below.

Figure 7:
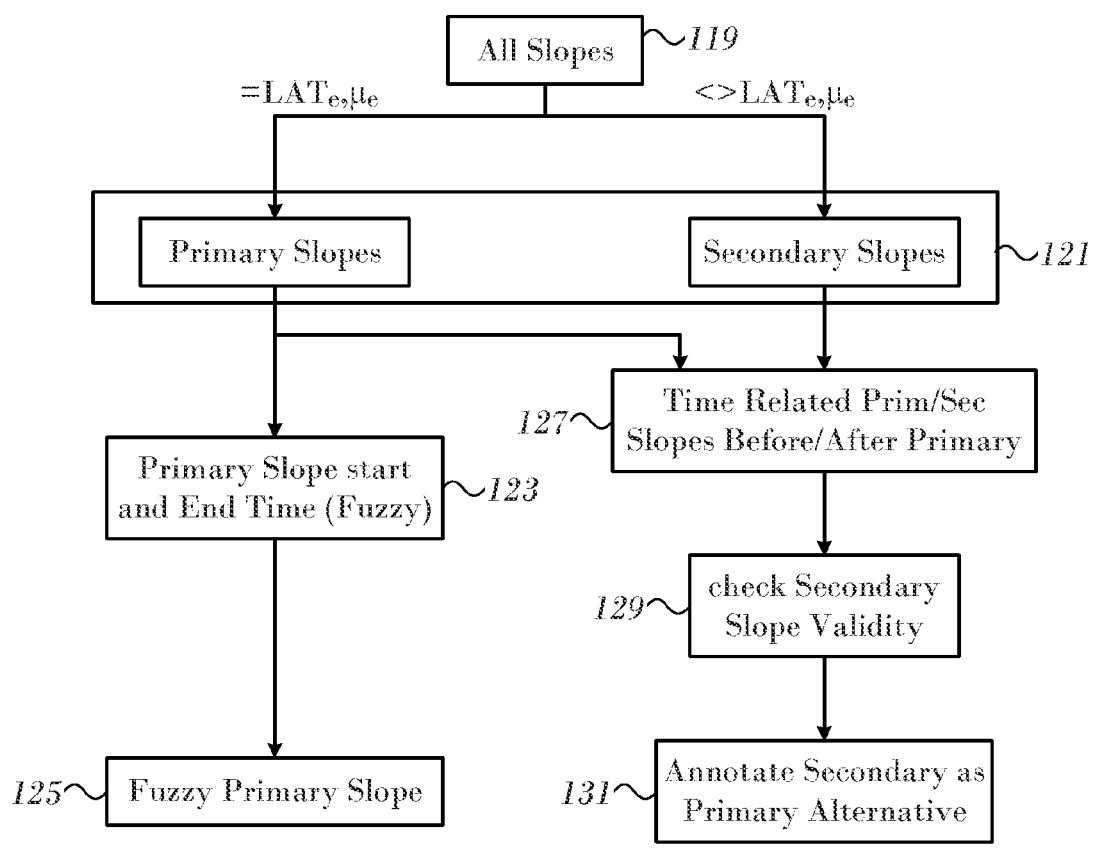
FIG. 7 is a flow chart of a method of LAT slope relation detection in accordance with an embodiment of the invention.

Reference is now made to FIG. 7, which is a flow chart of a method of LAT slope relation detection in accordance with an embodiment of the invention. In initial step 119 all slopes in the intracardiac electrograms are detected and denotched. Next, at step 121 a check is made for coincidence of the detected slopes with already detected LATs. When a coincidence is found, it is concluded that a current detected slope is a primary slope. Failure to find a coincidence implies that the current detected slope is a secondary slope.

At step 123 the start and end times of the primary slopes are determined. This determination is often imprecise, as the slopes may not be well demarcated. Such slopes are noted in final step 125 as "fuzzy primary slopes".

The time relationships between primary slopes and secondary slopes that were classified in step 121 are evaluated in step 127. It is noted whether the secondary slopes precede or follow the primary slopes, generally within a 30 ms window of interest, and a check is made to confirm validity of the secondary slope in step 129 their relationship to one another. Criteria for validity are:

slope amplitude>primary slope amplitude/2; and slope Time<primary slope time*2.

In final step 131 a secondary slope may be annotated as an alternative to a primary slope. This occurs when a secondary slope is coupled to primary slope and the secondary slope is valid, i.e., the slope is above a predefined threshold.

Figure 8:
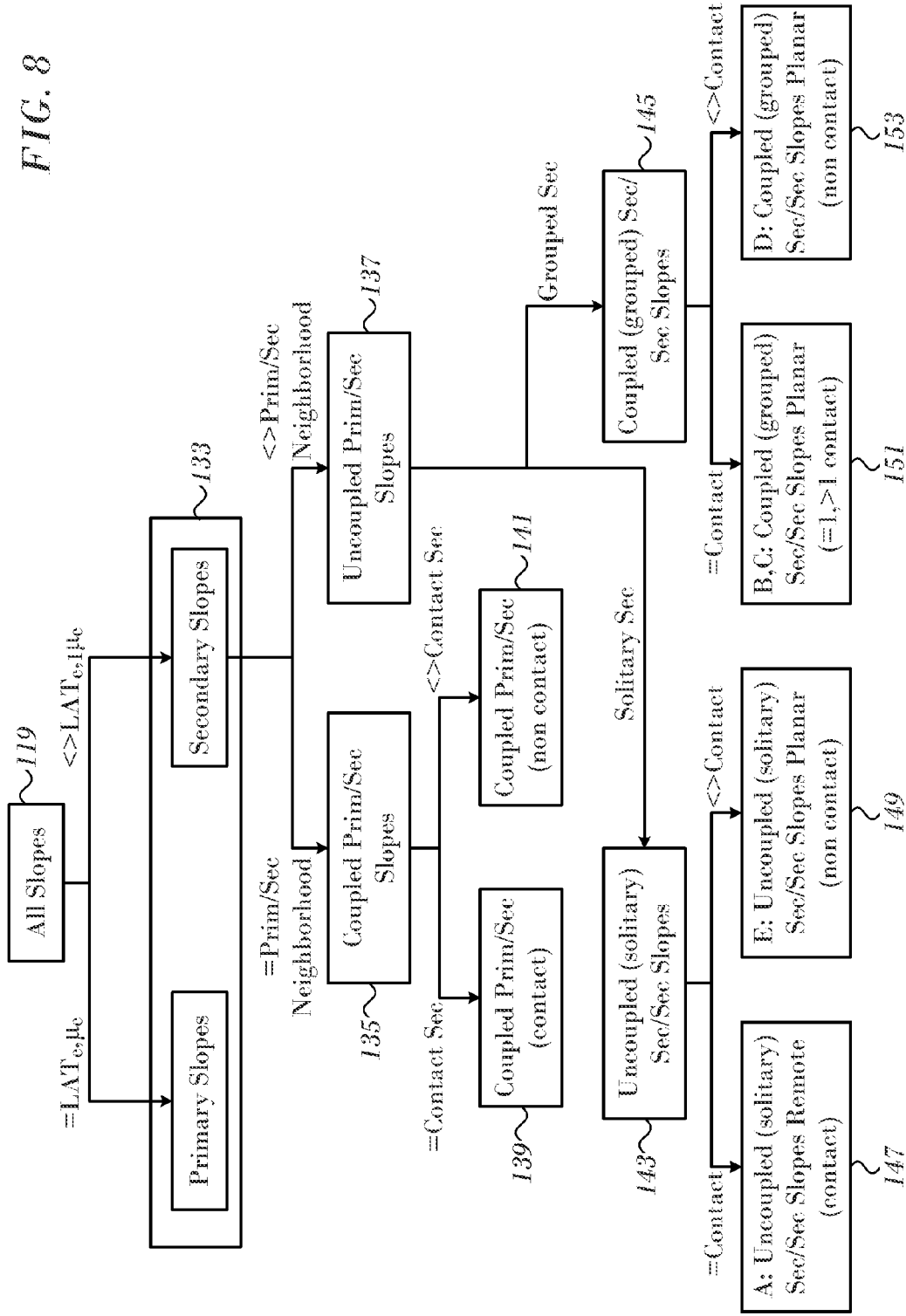
FIG. 8 is a detailed flow chart of a method of LAT slope relation detection in accordance with an embodiment of the invention.

Reference is now made to FIG. 8, which is a detailed flow chart of a method of LAT slope relation detection in accordance with an embodiment of the invention. Initial step 119 is carried out as in FIG. 7. In step 133 by looking at readily identified LAT annotations, primary slopes are identified in which there is a neighboring secondary slope, e.g., a secondary slope in another electrode in a 3×3 grid or within a predetermined distance from the electrode producing the primary slope. Secondary slopes are identified in which there is no neighboring primary slope by their lack of a close relationship to an LAT annotation. In steps 135, 137 the slopes are segregated into coupled primary-secondary slope pairs and uncoupled slopes, respectively. Both primary and secondary slopes are included in the latter category.

Proceeding from step 135, in steps 139, 141 the coupled primary-secondary slope pairs are further divided into groups in which the electrodes thereof are contacting and non-contacting with endocardium, respectively. A coupled primary-secondary slope combination exists when the electrode from which the secondary slope is read is in contact with the endocardium. This implies a conduction block.

Proceeding from step 137, in steps 143, 145 respectively, the uncoupled primary slopes and secondary slopes are further divided into solitary secondary slopes and grouped (coupled) secondary slopes.

Proceeding from step 143, in steps 147, 149 respectively, the uncoupled secondary slopes are segregated into a group in which a remote electrode with which they are associated is in contact with the endocardium and another group in which there is no such contact. In step 147 a contacting electrode indicates a missed activation, i.e., an activation in which a primary slope was not detected. In the case of step 149 no information can be derived. Sources other than an undetected activation wave, such as far field interference, may be responsible.

Proceeding from step 145, in steps 151, 153 respectively, the coupled secondary slopes are segregated into a group in which a remote electrode with which they are associated is in contact with the endocardium and another group in which there is no such contact. The significance of the notation "=1, >1 contact" in step 151 is given in FIG. 9. In both steps 151, 153 there is probably a missed activation. Localization of the position of virtual activation may differ in the cases of steps 151, 153.

Figure 9:
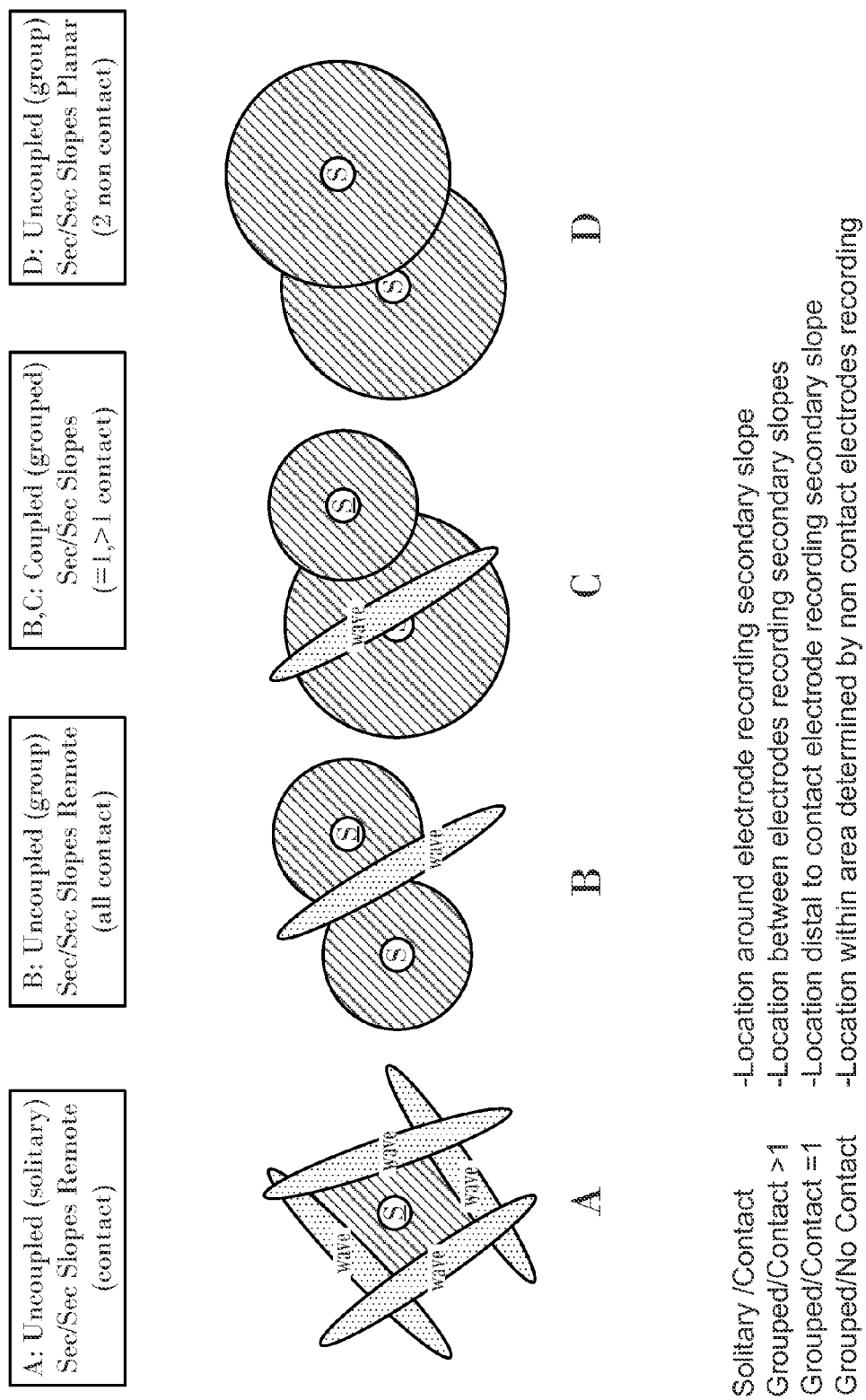
FIG. 9 graphically illustrates relations between the categories of secondary slopes identified in FIG. 8 and wave propagation configurations in accordance with an embodiment of the invention.

Reference is now made to FIG. 9, which graphically illustrates relations between the categories of secondary slopes identified in FIG. 8 and wave propagation configurations in accordance with an embodiment of the invention. Letter identifiers (A-D) within the blocks of FIG. 9 correlate with those in steps 147, 149, 151, 153 (FIG. 8). Individual cases shown in FIG. 9 follow:

Reference is now made to FIG. 10, which is a diagram illustrating detailed relations between coupled primary and secondary slopes detected by electrodes under different conditions, in accordance with an embodiment of the invention. The electrodes that recorded an intracardiac electrograms having secondary slope 155 coupled to primary slope 157 are not in contact with the endocardium. This situation suggests that the primary slope and secondary slope probably originated from the same propagation wave.

Reference is now made to FIG. 11, which is a diagram similar to FIG. 10 in accordance with an embodiment of the invention, but now the electrodes that recorded an intracardiac electrograms having secondary slope 159 coupled to primary slope 161 are in contact with the endocardium. This situation indicates a line of block 163 between the two electrodes within the slope time window.

Reference is now made to FIG. 12, which is a diagram similar to FIG. 10 in accordance with an embodiment of the invention. A wave pattern is described in a case two solitary, uncoupled electrodes showing secondary slopes. Both electrodes are in contact with the endocardium. The pattern indicates that a wave occurring near the electrode may have been missed.

Reference is now made to FIG. 13, which is a diagram similar to FIG. 10 in accordance with an embodiment of the invention. A wave pattern is described in a case of two solitary, uncoupled electrodes showing secondary slopes. Neither electrode is in contact with the endocardium. The pattern shown may indicate an artefact, e.g., ventricular far field effect or noise.

Reference is now made to FIG. 14, which is a diagram similar to FIG. 10 in accordance with an embodiment of the invention. This is a case in which at least two recording electrodes have coupled secondary slopes but are not coupled to a primary slope. The primary slope of a narrow wave 165 propagating between two electrodes failed to be detected in the signals from the electrodes.

Reference is now made to FIG. 15, which is a diagram similar to FIG. 10 in accordance with an embodiment of the invention. Two recording electrodes have coupled secondary slopes. Only one electrode is in contact with the endocardium. Neither electrode is coupled to a primary slope. This is consistent with a relatively broad wave 167, i.e., broader than the wave 165 (FIG. 14), which is propagating distal to the contacting electrode, and has failed to be detected by the electrodes.

Reference is now made to FIG. 16, which is a diagram similar to FIG. 10 in accordance with an embodiment of the invention. At least two uncoupled electrodes have detected secondary slopes. None is in contact with the endocardium, and none is coupled to a primary slope. However time-shifted primary slopes are available. This pattern suggest a current non-contact state among a set of electrodes in a larger are area, some of which were previously in contact with the endocardium.

Detected coupled primary slopes and secondary slopes in the case of a contacting electrode and another electrode that detects a secondary slope suggests a block between the electrodes. When the electrode that detects a secondary slope is not in contact with the endocardium, both primary and secondary slopes were probably produced by the same wave.

In the case of uncoupled electrodes detecting primary and secondary slopes, when the electrode that detects a secondary slope is in contact with the endocardium, a wave occurring near the electrode may have been missed. When the electrode that detects a secondary slope is not in contact with the endocardium, an artifact may be responsible.

In the case of multiple electrodes detecting secondary slopes, when at least one of them is in contact with the endocardium, a wave propagating between the secondary slopes recorded by the contacting electrode may have been missed.

When exactly one of the multiple electrodes is in contact with the endocardium, a wave propagating distal to the contacting electrode may have been missed.

When none of the multiple electrodes is in contact with the endocardium, waves may have been missed due to non-contact of neighboring electrodes with the endocardium in a larger area than the current 3×3 grid.

Confirmation of a wave block may be based on far-field information, depending on whether primary or secondary slope information is available. A finding of secondary (FF) slopes within the detected primary, (NF) slope window increases the likelihood of the existence of a wave block. The procedure for block line processing involves the following steps, which are explained in further detail below. The steps are not necessarily performed in the order listed:

Resolve isolated block points. This is done by revisiting all 'block points', to confirm isolation, i.e., absence of a block in surrounding electrodes.

Resolve closed block point areas around one or more electrode. This is done by identifying or failing to identify annotations in neighboring electrodes.

Interpolate block points into block lines.

Detection of Activation Block

Activation blocks are revealed by evaluation of conduction velocity vectors. Reference is now made to FIG. 17, which is a data flow chart illustrating the determination of conduction velocity vectors in accordance with an embodiment of the invention. Triangles are defined in a grid of electrode positions in block 169 The grid configuration is input as a signal 171 (ECONF), which outputs a signal 173 that represents the triangles. The signal 173 and signals 175, 177 representing LAT and LAT quality (LATQ) form inputs to block 179, in which LAT values from the electrodes of the triangles are determined. An output signal 181 from block 179 is received in block 183, where time-varying conduction velocity vectors are calculated within the triangles. Block 183 produces output signals 185, 187 comprising two vectors $CV_{earlier}$ and $CV_{later}$. The two vectors are analyzed in block 189 and a conduction velocity vector is produced in an output signal 191, together with a measure of quality (CVQ), Ø (a vector normal to the activation front and a parameter Ψ, which is a conduction velocity vector in 3-dimensional space. The details of calculating conduction velocity vectors are described in further detail in the discussion of FIG. 22 below.

Figure 18:
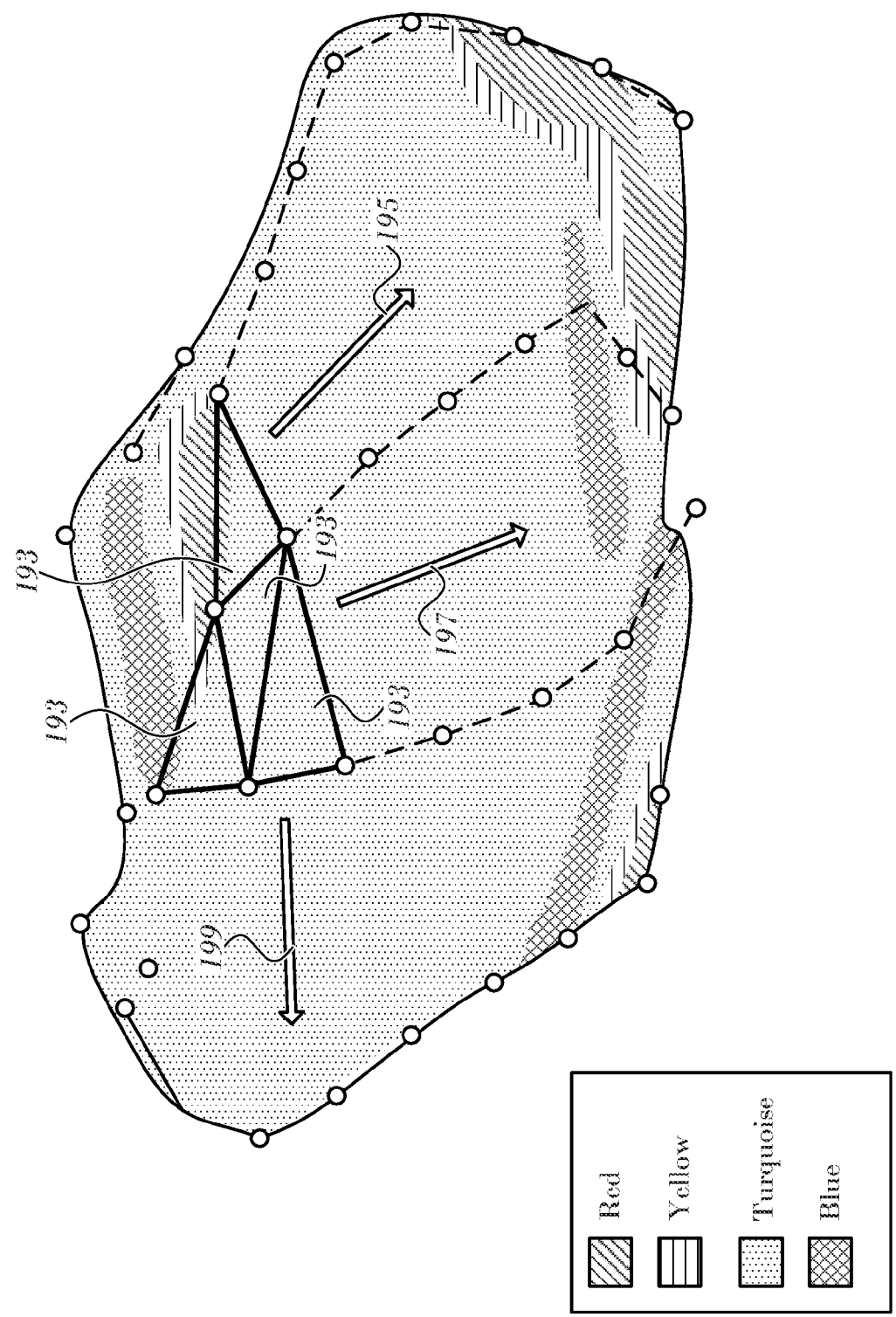
FIG. 18 is a functional electroanatomic map of the heart illustrating conduction velocity vectors in accordance with an embodiment of the invention.

Reference is now made to FIG. 18, which is a functional electroanatomic map of the heart illustrating conduction velocity vectors produced according to the arrangement of FIG. 4, in accordance with an embodiment of the invention. A set of numbered electrodes defines triangles 193. Local activation times are indicated by a key in the figure. Three conduction velocity vectors 195, 197, 199 are shown.

Figure 19:
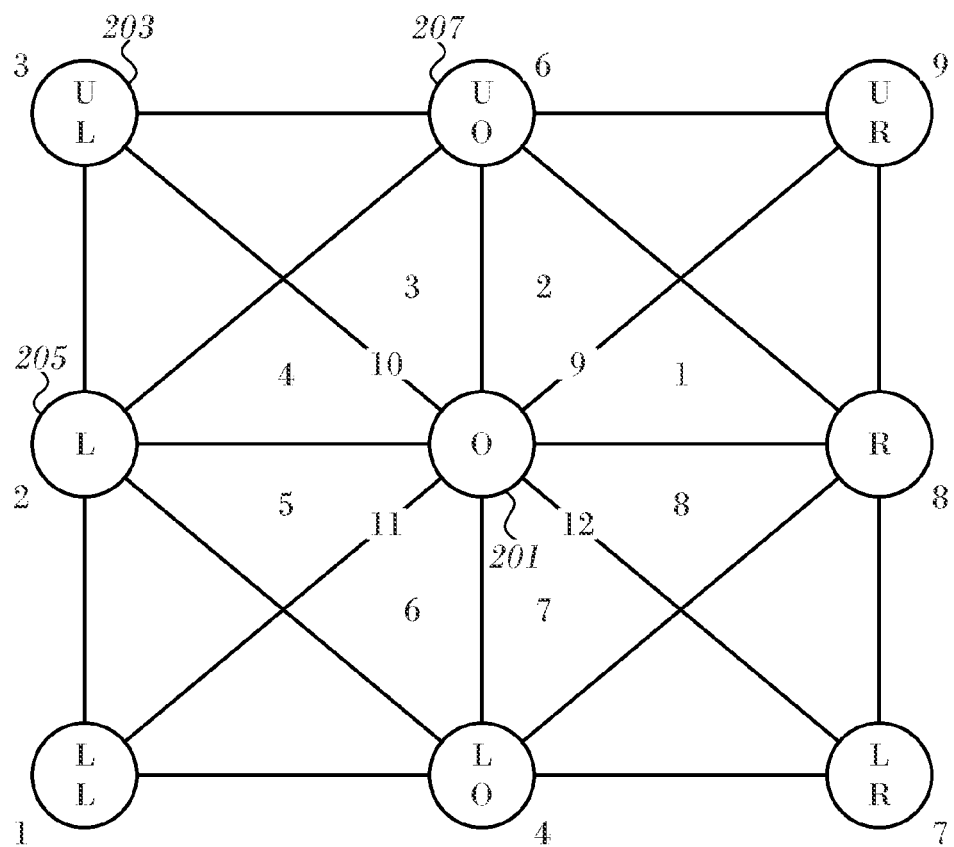
FIG. 19 is a square grid of nine electrodes, which are processed in accordance with an embodiment of the invention.

Reference is now made to FIG. 19, which is a square grid of nine electrodes, which are processed in accordance with an embodiment of the invention. Inspection of FIG. 19 reveals that 12 triangles share a pivot electrode 201. For example, one triangle is defined by pivot electrode 201 and vertex electrodes 203, 205. Another triangle is defined by pivot electrode 201 and vertex electrodes 205, 207. Each of the 12 triangles has two vertex electrodes that are shared with neighboring triangles.

Reference is now made to FIG. 20, which is a representative series of three electrograms 209, 211, 213 from electrodes defining a triangle in the grid of FIG. 19 in accordance with an embodiment of the invention. The triangles may be any of the triangles shown in FIG. 19. Electrogram 211 is from the pivot electrode 201. Detection of an activation block comprises determining the LAT for the pivot and vertex electrodes, and determining the 3-dimensional distance between the vertices of the triangle. The conduction velocity vector in the signal 191 (FIG. 17) is used as a parameter for block detection.

Figure 21:
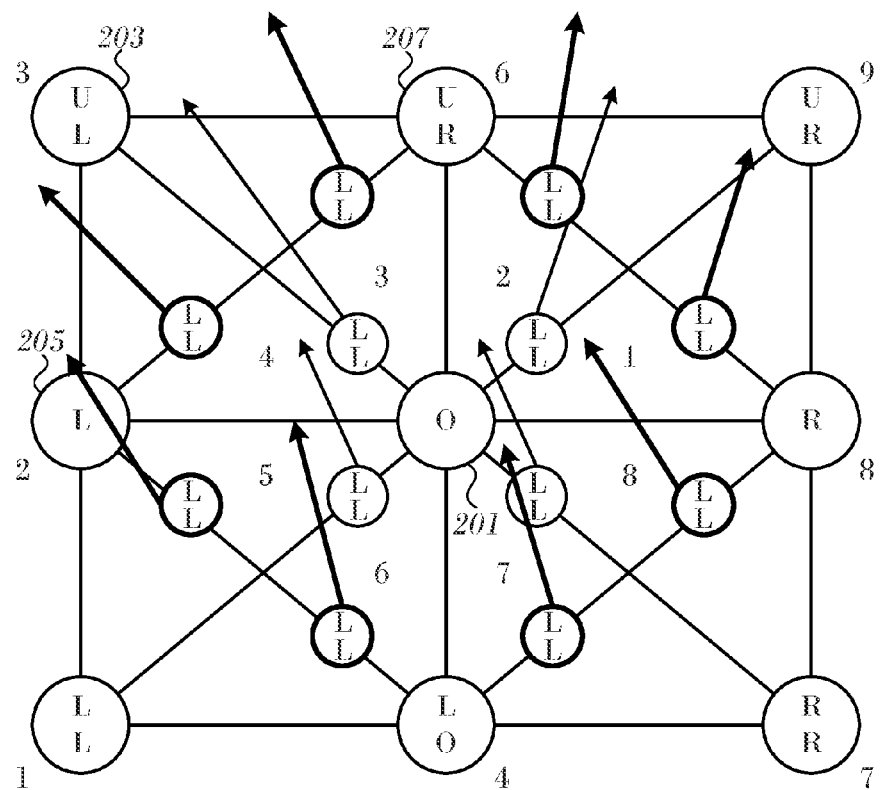
FIG. 21 is a square grid of nine electrodes illustrating conduction velocity vectors, in accordance with an embodiment of the invention.

Reference is now made to FIG. 21, which is a square grid of nine electrodes similar to FIG. 19, illustrating conduction velocity vectors, in accordance with an embodiment of the invention. Four conduction velocity vectors can be calculated for each of the triangles. In the case of a single triangle 3×2=6 activation times are available from neighboring electrodes in the grid Different combinations of 2×2=4 of the neighboring activation times and a selected LAT from one corner of the triangle provide a set of four conduction velocity vectors. One of the four conduction velocity vectors is chosen. Conduction velocity vectors outside boundaries of conduction block (<0.2 m/s) and non-physiological simultaneous activation (>2 m/s) are discarded in favor of conduction velocity vectors within the boundaries From the latter the conduction velocity vector having the largest magnitude is chosen. The chosen conduction velocity vectors are shown as beginning in the triangle's center of gravity, denoted on a rectangular coordinate system as $x_c$, $y_c$.

Figure 22:
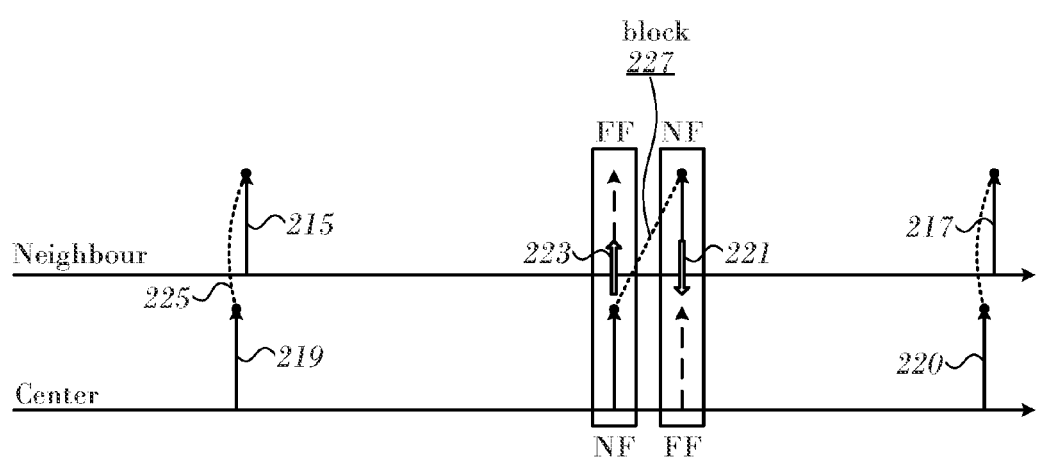
FIG. 22 is an example showing annotation results from an electrode at the center of a 3×3 grid and a neighboring electrode in the grid in accordance with an embodiment of the invention.

Reference is now made to FIG. 22, which is an example showing annotation results from an electrode at the center of a 3×3 grid and a neighboring electrode in the grid in accordance with an embodiment of the invention. Solid arrows 215, 217, 219, 220 indicate annotations based on primary activations. Arrows 221, 223, shown in broken lines, indicate activations related to secondary slopes. A time relation exists between the primary annotations, e.g., arrow 215, 219 (indicated by a connection by broken line 225), indicating propagation between the two electrodes and that the two primary slopes defining the primary annotations are coupled.

In the case of the annotations represented by arrows 223, 227 the dissociation of the two conduction velocity vectors indicates a conduction block 227.

Region Growing

Figure 23:
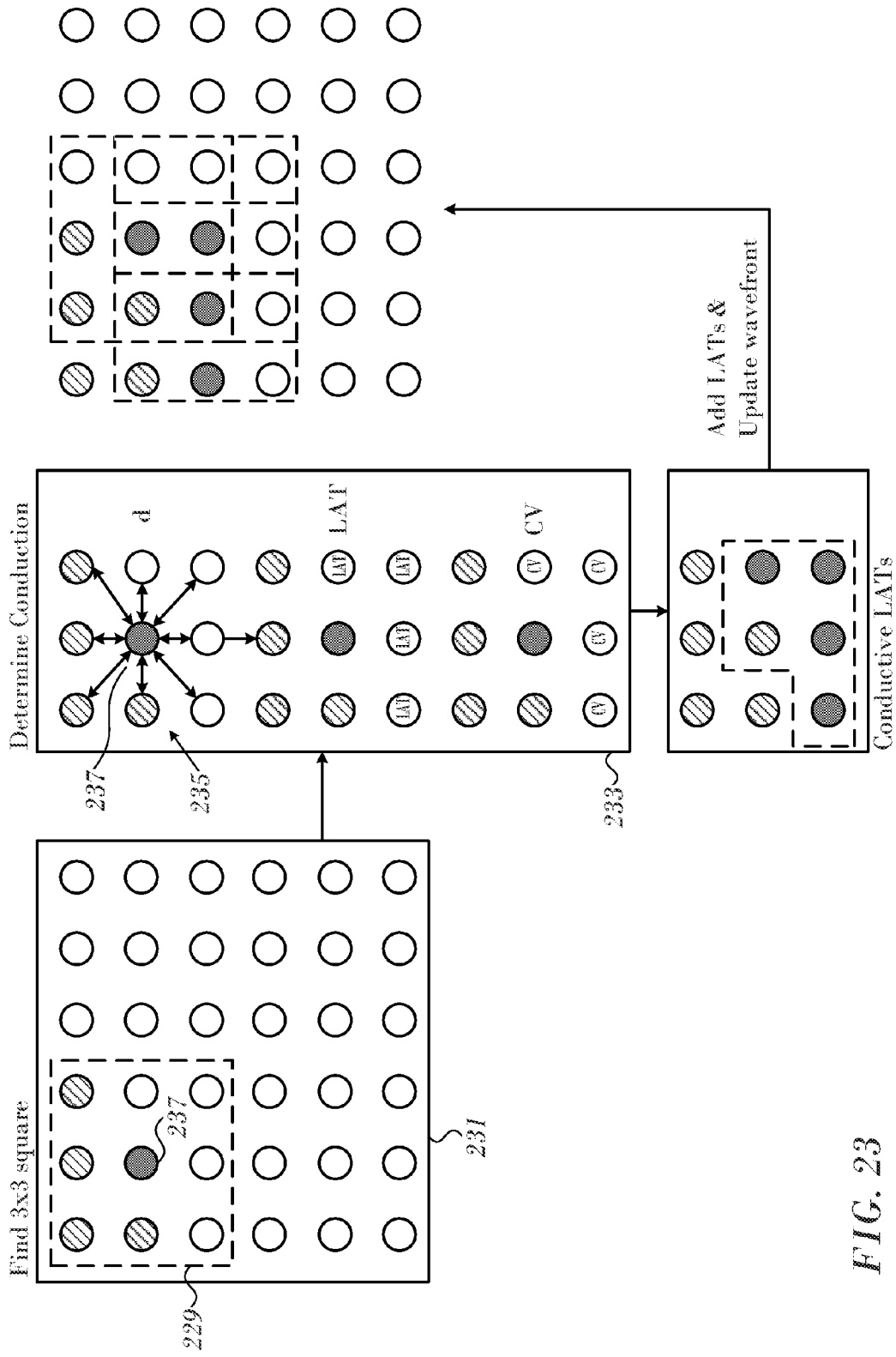
FIG. 23 is a diagram explaining a process of region growing, in accordance with an embodiment of the invention.

Detection of atrial fibrillation waves by an electrode mesh involve a region growing algorithm and a frame generation and segmentation algorithm. Reference is now made to FIG. 23, which is a diagram explaining a process of region growing, in accordance with an embodiment of the invention. The process is iterative. It is convenient to identify neighboring electrodes around the center of a 3×3 grid, e.g., by numbers. For purposes of region growing a normalized conduction velocity is calculated, using the LATs of the center electrode and the eight neighboring electrodes in the 3×3 grid.

A 3×3 square grid 229 of electrodes is identified in block 231, shown as a square delineated by a broken line.

Next, in block 233 conduction is evaluated in the square grid 229 at stage 235. This process requires:

(1) calculating the 3-dimensional distance between center electrode 237 and neighboring electrodes in the square grid 229;

(2) determining the local activation time interval between the center electrode 237 and the neighboring electrodes, Additional information is available for extension of the region:

(1) LAT time windows. These provide indications of LAT inaccuracy.

(2) Conduction velocity vector of four 2×2 squares within the 3×3 grid.

(3) A primary annotation and FF slope (secondary annotation) for neighboring IC-ECG.

(4) Quality of the IC-ECG and the LAT quality.

Conduction integrity or a conduction block may now be determined based on $CV_{norm}=d(LAT)/d(LOC)$, where LOC refers to the location of an intracardiac electrode $CV_{norm} \geq CV$.

A block is indicated when $CV_{norm} \leq CV_{norm\_min}$, in which case $CV \leq CV_{norm\_min}$.

An alternative conduction detection strategy includes determining the magnitude of conduction velocity vector only for high quality IC-ECGs and LATs. This method suffers from sensitivity to LAT inaccuracies.

Another alternative conduction detection strategy involves fitting a 3×3 fit of a bi-quadratic surface on LATs using standard methods. This results in an over-determined solution, but is more robust against LAT inaccuracies.

Frames

Figure 24:
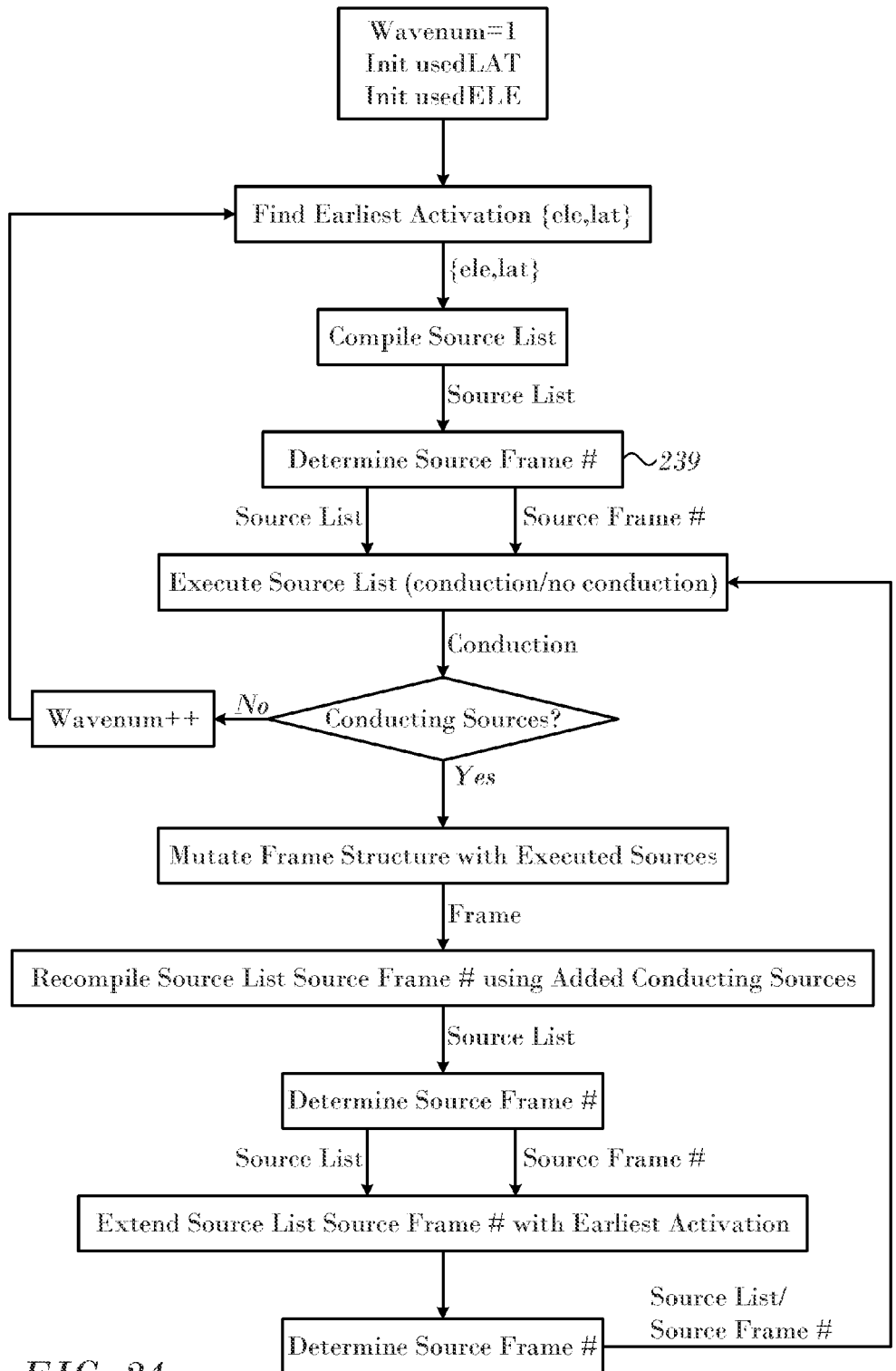
FIG. 24 is a flow diagram illustrating frame segmentation in accordance with an embodiment of the invention.

Reference is now made to FIG. 24, which is a flow diagram illustrating the details of block 49 (FIG. 2). The diagram describes frame segmentation in accordance with an embodiment of the invention. Frames are filled with LATs that most logically relate to each other. Within this process, conduction velocity is calculated. Conduction blocks are determined by reference to corresponding LATs in subsequent frames.

A source list is maintained during the course of execution of the algorithm. The source list contains electrode numbers and associated LATs to be checked against neighboring LATs for block or conduction. Electrode numbers that are found to be conductive are added to the source list and checked in the next run of the algorithm. In this way, the algorithm grows a region of electrode numbers that belong to the same wave.

A source frame is determined in block 239. The input to this block is the frame structure, a distance matrix and the LAT obtained from the source electrode. The output of block 239 is the frame number for the source electrode. Assignment of a frame number is based on vacancy of frames at the LAT of the source electrode. For all vacant frames the following characteristics are calculated in order to support an assignment decision, using Matlab routines as shown in Table 2.

TABLE 2

| Characteristic | Matlab Vector (Unit) |
|---|---|
| Determine vector of vacant frame(s)<br>1 = Frame is vacant at source electrode position<br>2 = Frame is already occupied at electrode position | vacantframes(1 |
| Calculate closest LAT vs. source electrode/LAT<br>1. Minimum \|dLAT\|between existing electrode/LAT and source LAT | closestLAT(ms) |
| Determine adjacency to already existing neighboring electrodes.<br>1 = solitary electrode, no neighbors<br>0 = neighbors around electrode available in frame(s) | solonele(0, 1) |
| Conduction or block situation<br>1 = Conduction to any of the neighboring electrodes<br>0 = No conduction to any of the neighboring electrode or when no neighboring electrodes available (i.e., when solonele = 1) | condnele(0, 1 |
| Maximum CV between source electrode neighboring electrodes<br>Number = Maximum CV between source electrode and one<br>NaN = When no neighboring electrodes are available | Maxcvnele (num, NaN) |

Based on the characteristics for each vacant frame the decision rules are given in pseudocode in Listing 1.

Listing 1

```
If no vacant frames are available
    Source {ele/LAT} is assigned to the next frame
elseif frames are available with one or more conducting first order
neighbor activation(s)
    Source {ele/LAT} is assigned to the frame with closest LAT
elseif no frames with conducting neighboring activation are available
    if closest LAT<100 ms(AF cycle)
        Source {ele/LAT} is assigned to the frame with closest LAT
    else
        Source {ele/LAT} is assigned to the next frame
    end
end.
```

Figure 25:
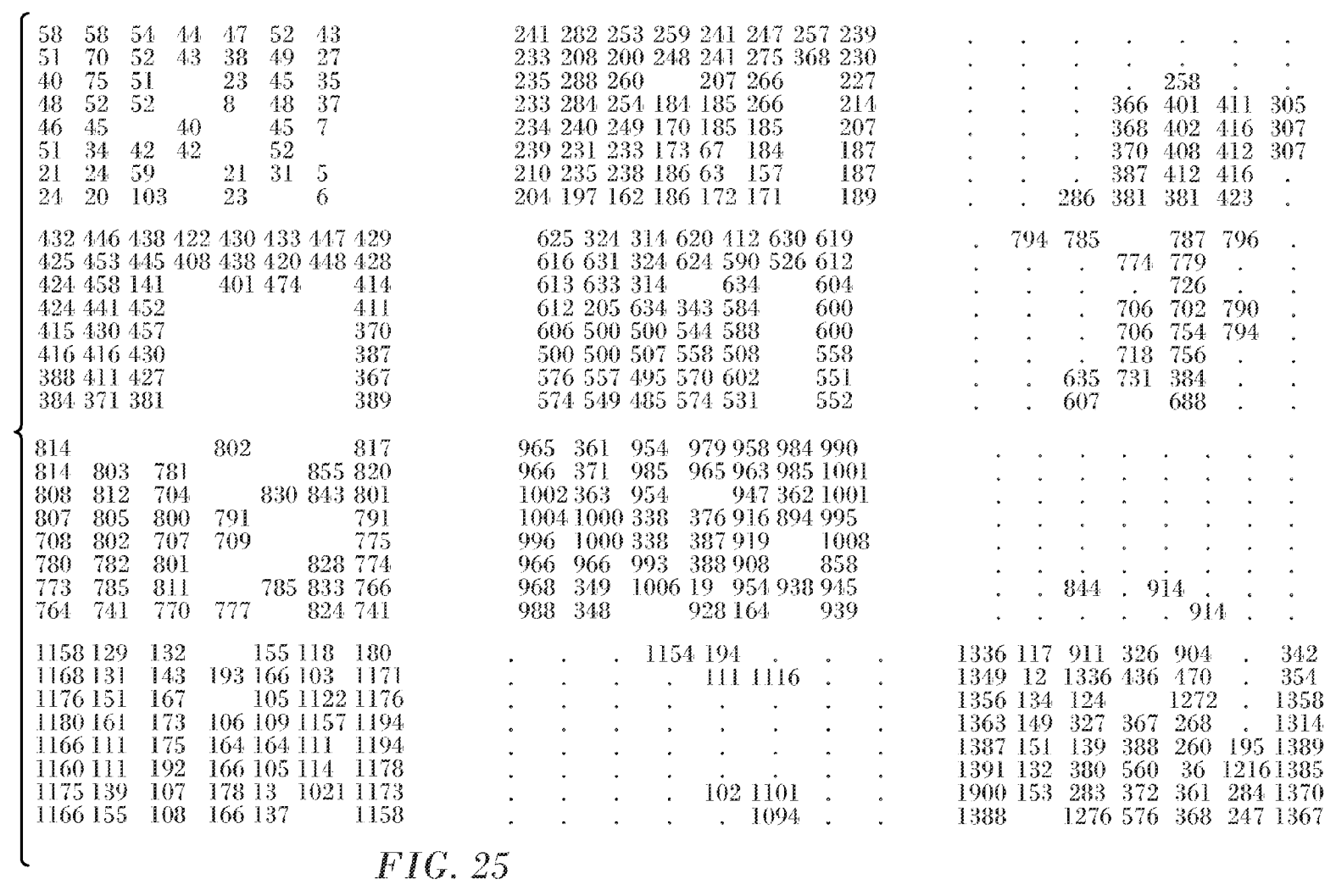

Reference is now made to FIG. 25, which is an exemplary frame segmentation map produced by the above-noted algorithm and Matlab routines, in accordance with an embodiment of the invention. Blank areas in the frames can be attributed to missing electrodes, or to a wave that resides in the next frame as a result of reassignment of values when there is an inter-wave block detected during the frame segmentation process.

Figure 26:
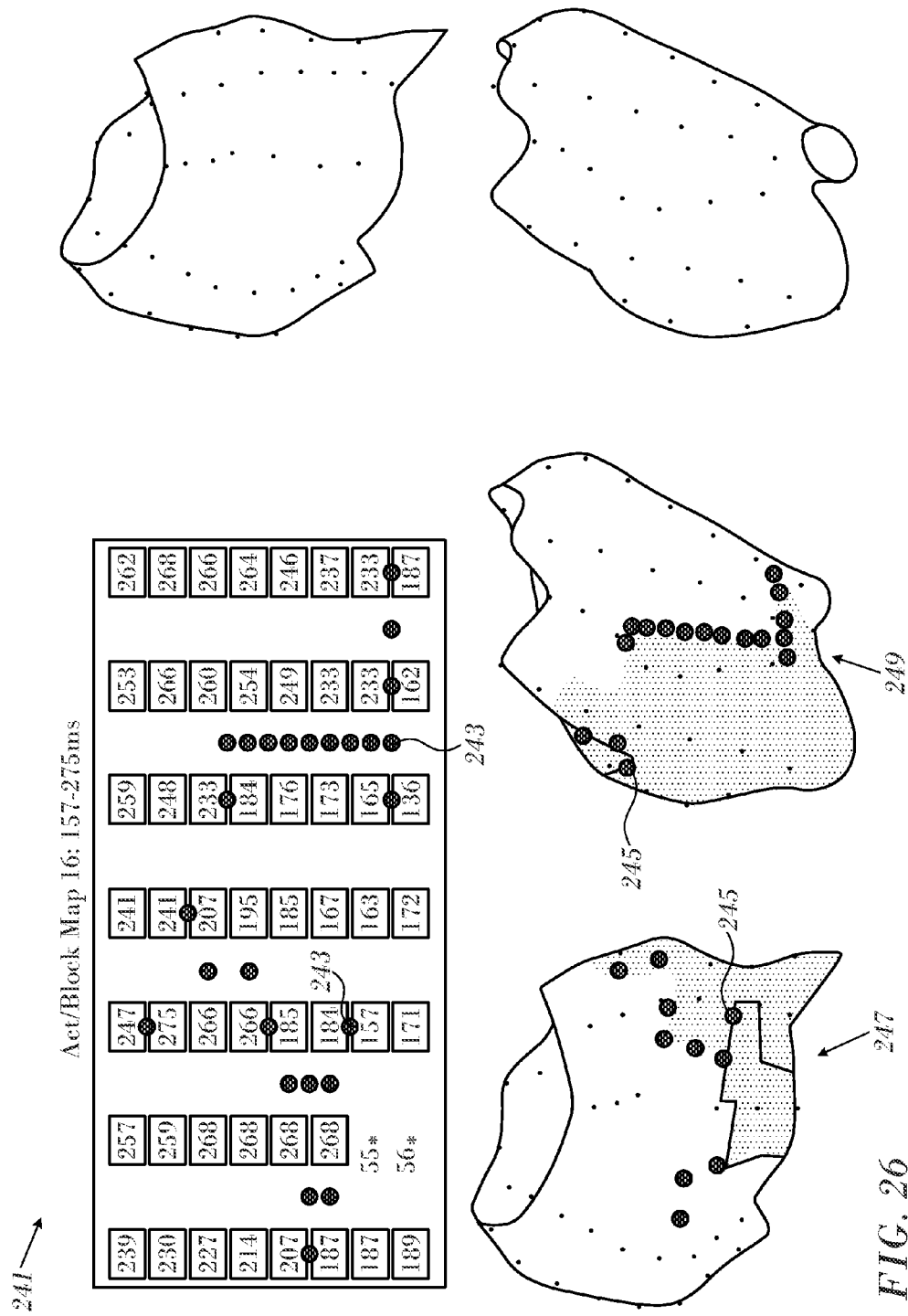
FIG. 26 is a composite diagram showing an exemplary frame segmentation matrix and electroanatomic maps produced by an embodiment of the invention.

As noted above in the discussion of block 51 (FIG. 2), it is possible to generate various functional electroanatomic maps and matrices from segmented frames: conduction map and matrix; activation map and matrix; block map; wave map; and conduction velocity map. Reference is now made to FIG. 26, which is a composite diagram showing an exemplary frame segmentation matrix 241 and electroanatomic maps produced by the above-noted algorithm and Matlab routines, in accordance with an embodiment of the invention. Lines of block are indicated by dots, e.g., dots 243 on the matrix 241 and dots 245 on maps 247, 249.

Wave Mapping: Post Processing

Post processing involves resolving the following configurations: isolated annotation waves; a small number of annotations; and islets of non-annotated areas within waves in some electrodes. The procedure comprises detecting inter-wave blocks, i.e., blocks along the wavefront, and detecting intrawave blocks, e.g., a "U-turn" in the propagation. Interpolation of block lines is then performed. The interpolation may involve creation of block lines by interpolating block points, and interpolate any gaps using electrogram data. Block line pattern analysis is typically done on the interpolation results as described below.

Post processing involves evaluation of each IC-ECG. This involves quality evaluation (episodes per sec), the number of annotations (NoAe), and a NoAe threshold: LOWACTELE*Number of waves. An IC-ECG is acceptable if NOAe>NOAe threshold.

Moreover, post processing is performed per annotation, with evaluation of the quality of the annotation (QoA), and a QoA threshold established: LOWAUTHR*mean (QoA). Annotations are acceptable if QoA>QoA threshold.

Post processing is performed on each wave, where the number of annotations per wave (NoAW) is determined. A NoAW threshold is established: (LOWACTWAVE*Number of accepted IC-ECG). Waves are accepted if NoAW>NoAW threshold.

The quality a wave activations (QoW) is evaluated. A QoW threshold is established: LOWWAVEQUALITY*mean (QoW Accepted waves). Wave activations are accepted if QoW>QoW threshold.

Resolving annotation waves involves revisiting all non-accepted waves, i.e., waves where NoAW NoAW threshold. There are three options to deal with annotations that are found within non-accepted waves:

(1) Merge the annotation with an overlapping accepted wave.

(2) Swap the annotation an overlapping accepted wave annotation, (dispose one of the two annotations).

(3) Dispose of the annotation

Block Processing

Block line filtering of waves and activation maps produces relatively robust block lines and wave maps compared with their unfiltered counterparts. The process includes detection of spurious block line points, which are typically isolated block points or small groups of block points. An example of spurious block points is presented below in FIG. 40.

Signals that result from block line filtering are useful for block line temporal analysis. Thus, block point and block line density relate to occurrences of the block per unit of time. Block point stability relates to the consistency of subsequent occurrences of the block. Block point repetition is a measure of the periodicity of repeated occurrences of the block lines In addition the filtering of block lines increases the usefulness of block line pattern analysis. In particular specific planar activations such as dissociated waves, collision and fusion of waves, and epicardial breakthrough and focus. Non-planar patterns, i.e., U-turn and rotor patterns are also analyzed. Filtering increases the ability to revisit and resolve isolated block points and block point areas around one or more electrodes. For example the LAT may be relocated within a time window to attempt to resolve the block. Interpolation of block points into easily visualized block lines can deal with missing block segments.

One display that may be generated using block line filtering is an electrode/block line matrix. Reference is now made to FIG. 27, which shows an exemplary 8×8 electrode block/line matrix 251 that is processed using template matching, in accordance with an embodiment of the invention. The matrix 251 can be processed by image-processing algorithms that may employ additional filtering for smoothing and noise reduction, template matching, and other types of feature recognition techniques.

A constellation (N=8, M=8) is connected in the matrix 251. More generally, N×M electrodes provide a block matrix of size:

$$(2N1+O_N) \times (2M-1+O_M),$$

where $O_N$ and $O_M$ are either 0 or 1, indicating no connection or one connection, respectively. Four templates 253, 255, 257, 259 are shown. A key in the lower part of the figure describes the meanings of the connections. Matches with the template 253 and template 257 are demonstrated in an encircled area 261.

Figure 28:
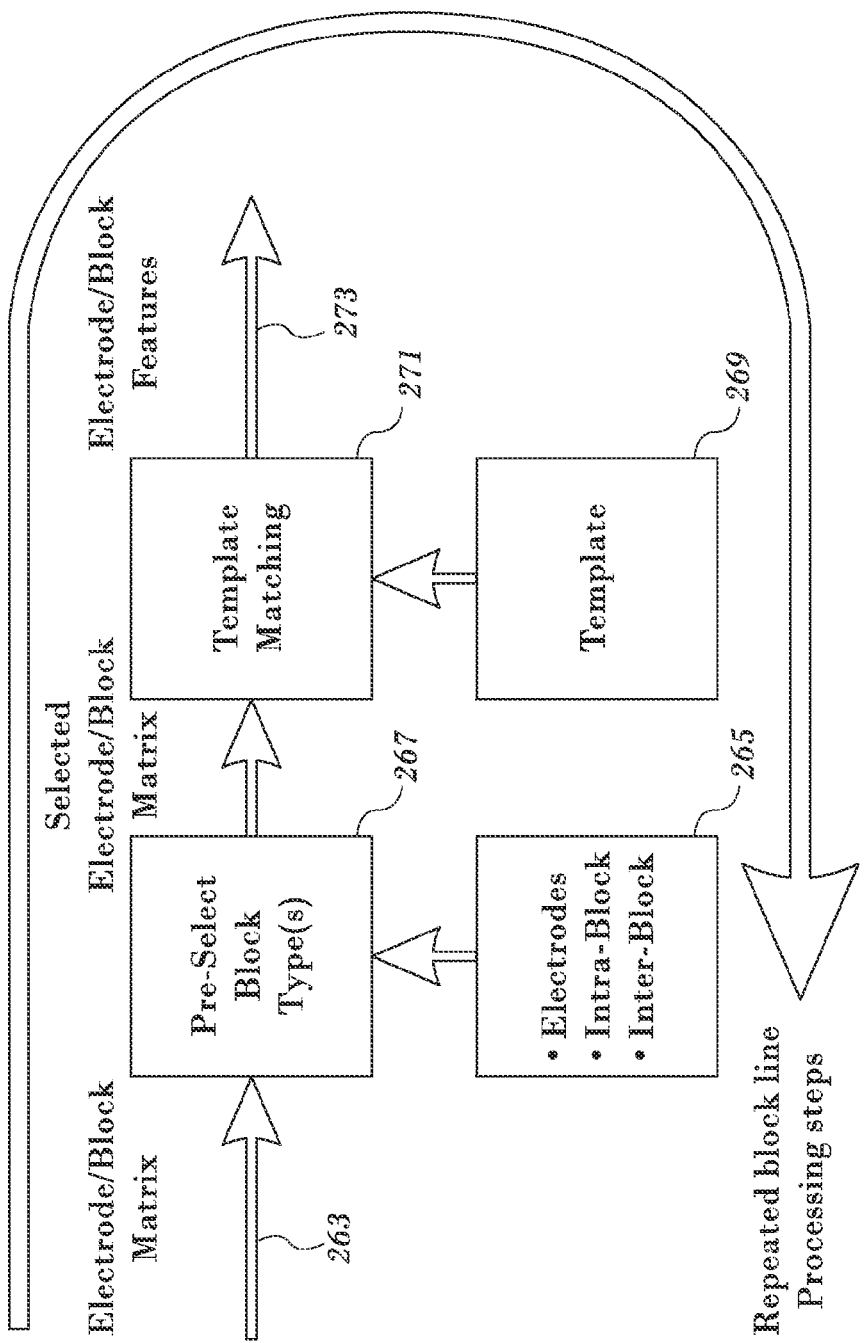
FIG. 28 is a flow diagram illustrating iterative processing of the matrix shown in FIG. 27 in accordance with an embodiment of the invention.

Reference is now made to FIG. 28, which is a flow diagram illustrating iterative processing of the matrix 251 (FIG. 27) in accordance with an embodiment of the invention. In a first phase, the matrix is input as signal 263. Electrodes relating to particular block propagation categories are identified in step 265, and the block propagation categories determined in step 267. Template matching for the categories is conducted in step 269, where a template library is referenced and templates from the library matched in step 271. Features of the block and the electrodes are output as signal 273.

Figure 29:
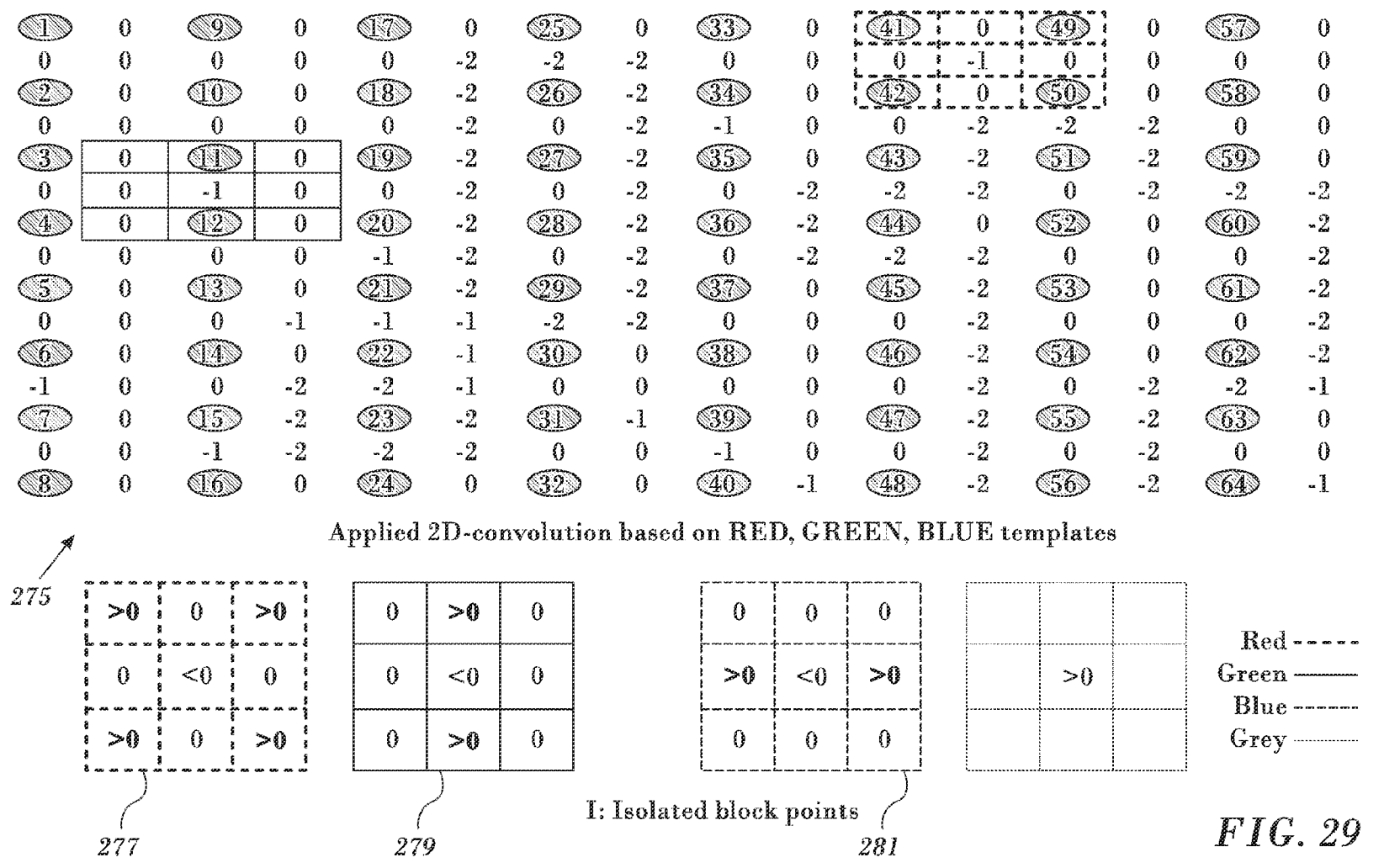

Reference is now made to FIG. 29, which shows a block-line matrix 275 that has been subjected to template matching in accordance with an embodiment of the invention. In this example 2-dimensional convolution has been applied, based on templates 277, 279, 281.

Figure 30:
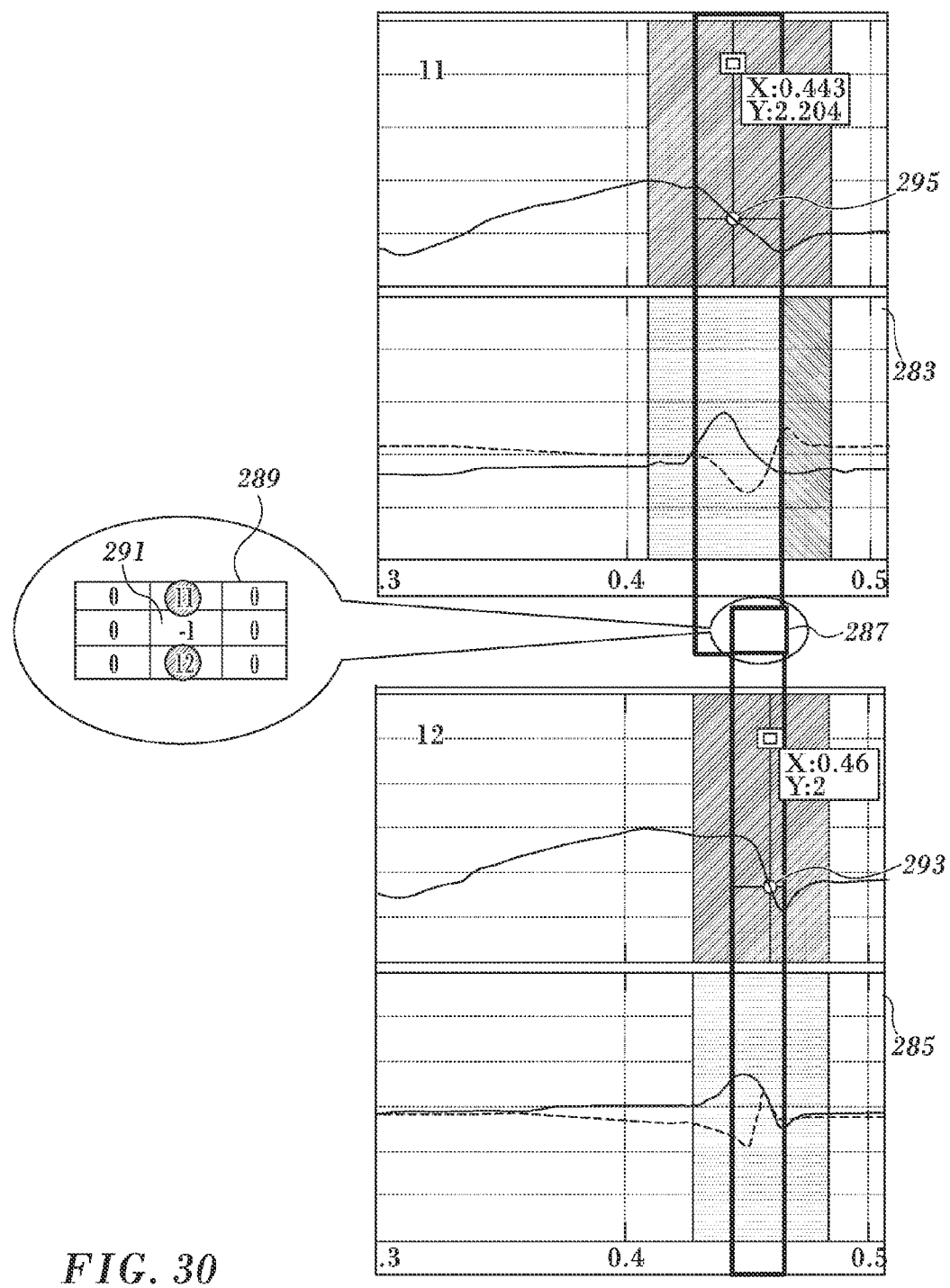
FIG. 30 is a composite diagram illustrating analysis of propagation in an electrode block line matrix in accordance with an embodiment of the invention.

Reference is now made to FIG. 30, which is a composite diagram illustrating analysis of electrograms 283, 285 and propagation in an electrode block line matrix 287 in accordance with an embodiment of the invention. A segment 289 of the matrix including electrodes 11 and 12 is enlarged in the balloon and indicates an isolated block point 291. Repositioning of annotations 293, 295 resolves the issue, and block point 291 may be removed (disposed) from the list of block points using the iterative procedures described above. This allows the block lines to be cleaned up.

Figure 31:
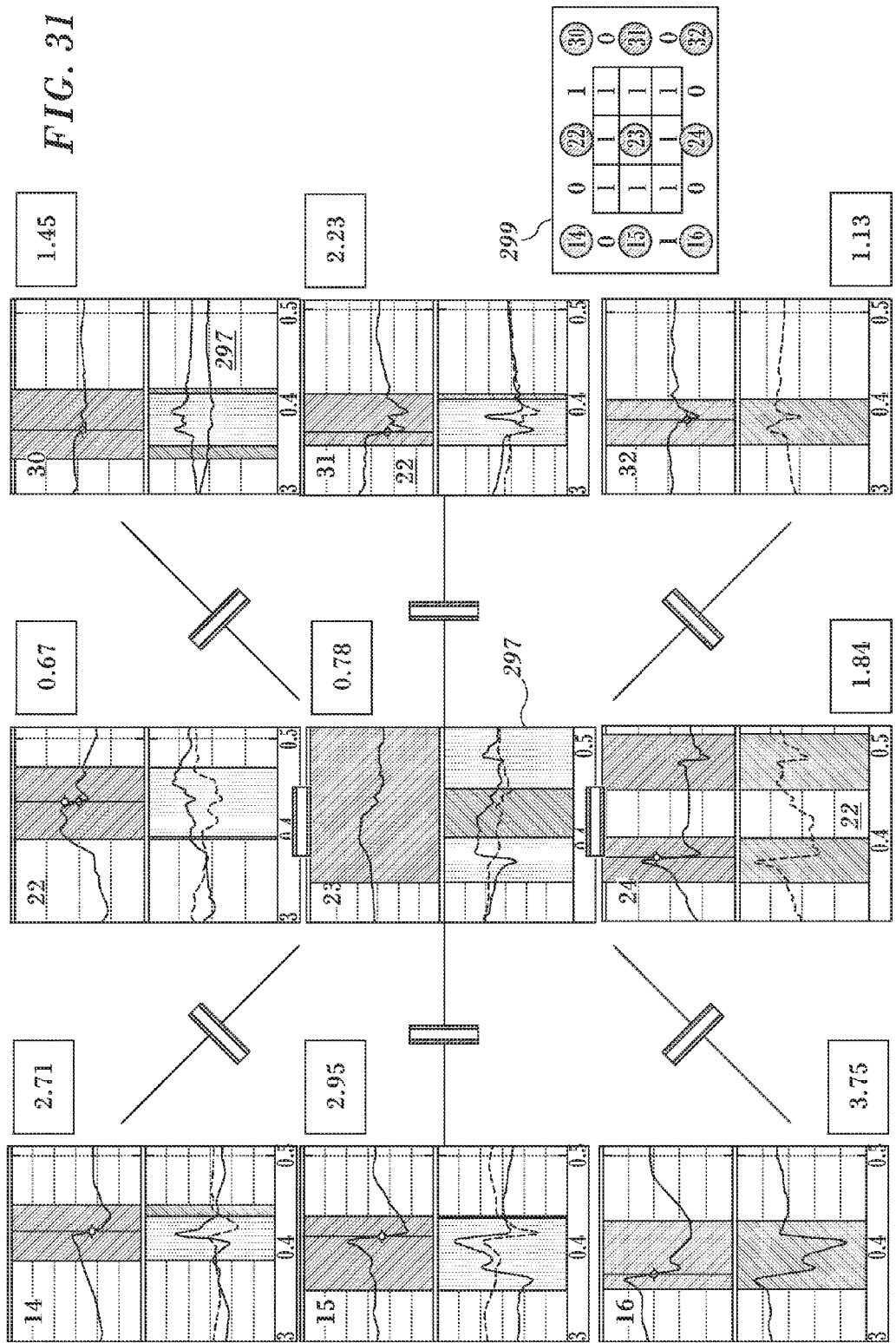
FIG. 31 is a composite diagram showing a series of electrograms, taken from a block line matrix in accordance with an embodiment of the invention.
Figure 32:
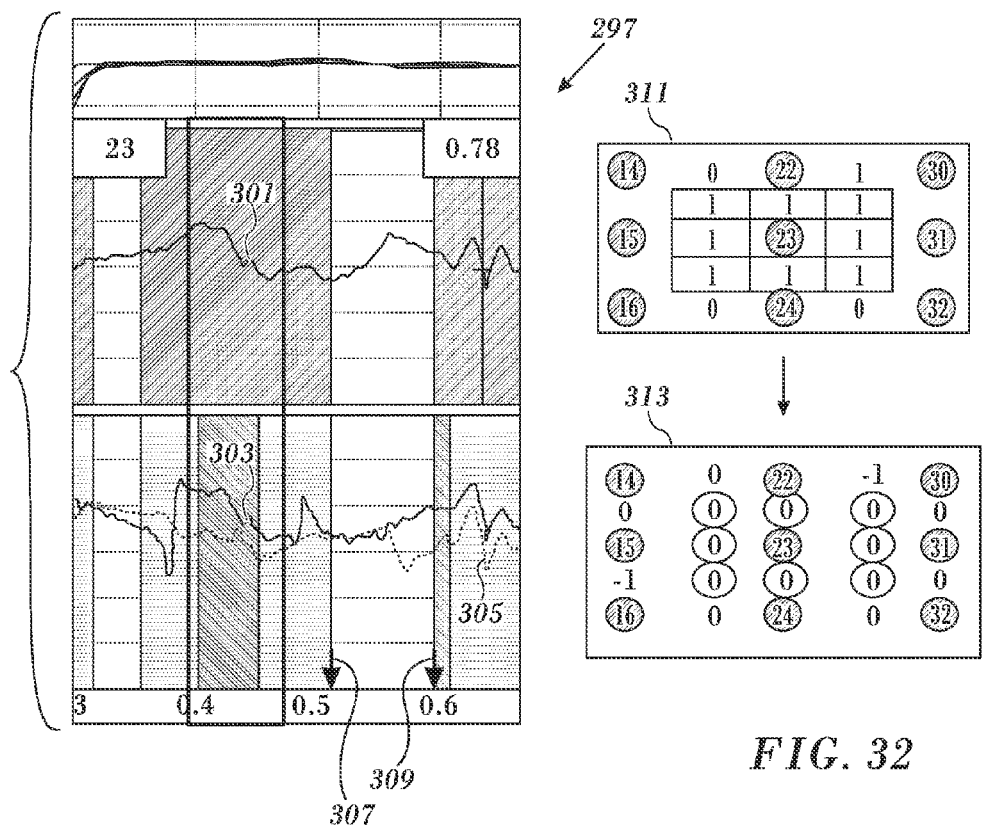
FIG. 32 is an enlarged version of an electrogram of FIG. 31), which is analyzed in accordance with an embodiment of the invention.

Reference is now made to FIG. 31, which is a composite diagram showing a series of electrograms, including electrogram 297 taken from a block line matrix 299, in accordance with an embodiment of the invention. FIG. 31 is a reference for the analyses of the matrix 299 which follow:

Reference is now made to FIG. 32, which is an enlarged version of electrogram 297 (FIG. 31), which is analyzed in accordance with an embodiment of the invention. Tracing 301 in the upper pane is a bipolar signal, which is the difference between unipolar tracings 303, 305 in the lower pane. The bipolar window is defined by arrows 307, 309. When there is low EGM quality removing EGM window will eliminated spurious block points. EGM quality is a compound parameter determined by a scoring algorithm that takes into consideration slope, noise, far-field effects, etc. The center of matched template entries in matrix segment 311 prior to processing can be set to zero (indicating absence of a conduction block) as shown in revised matrix segment 313.

Figure 33:
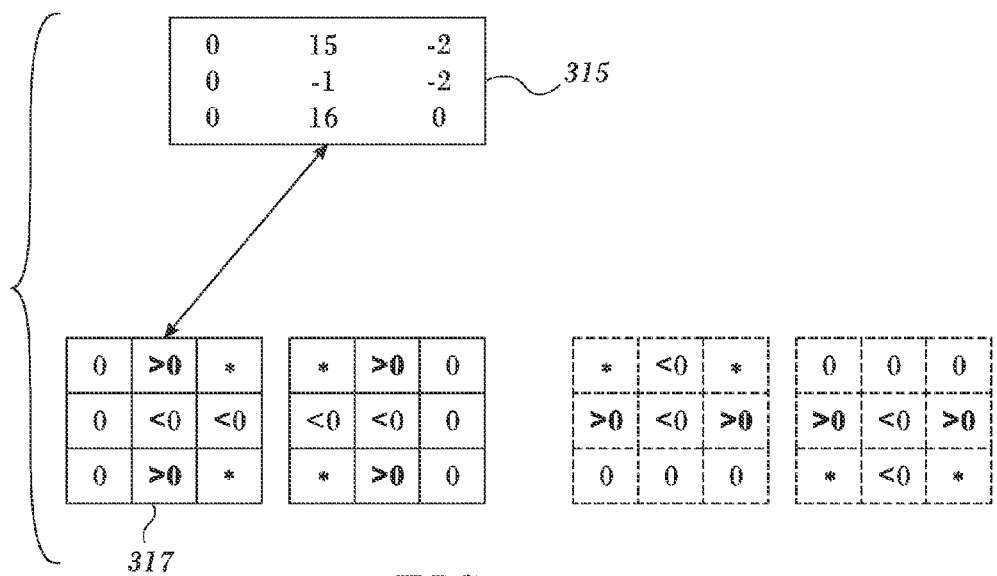
FIG. 33 is a composite diagram showing template matching with a matrix segment in accordance with an embodiment of the invention.

Reference is now made to FIG. 33, which is a composite diagram showing template matching with a matrix segment 315, in accordance with an embodiment of the invention. There is a match between the matrix segment 315 and template 317. The example shows a detour block line.

Temporal Analysis

Figure 34:
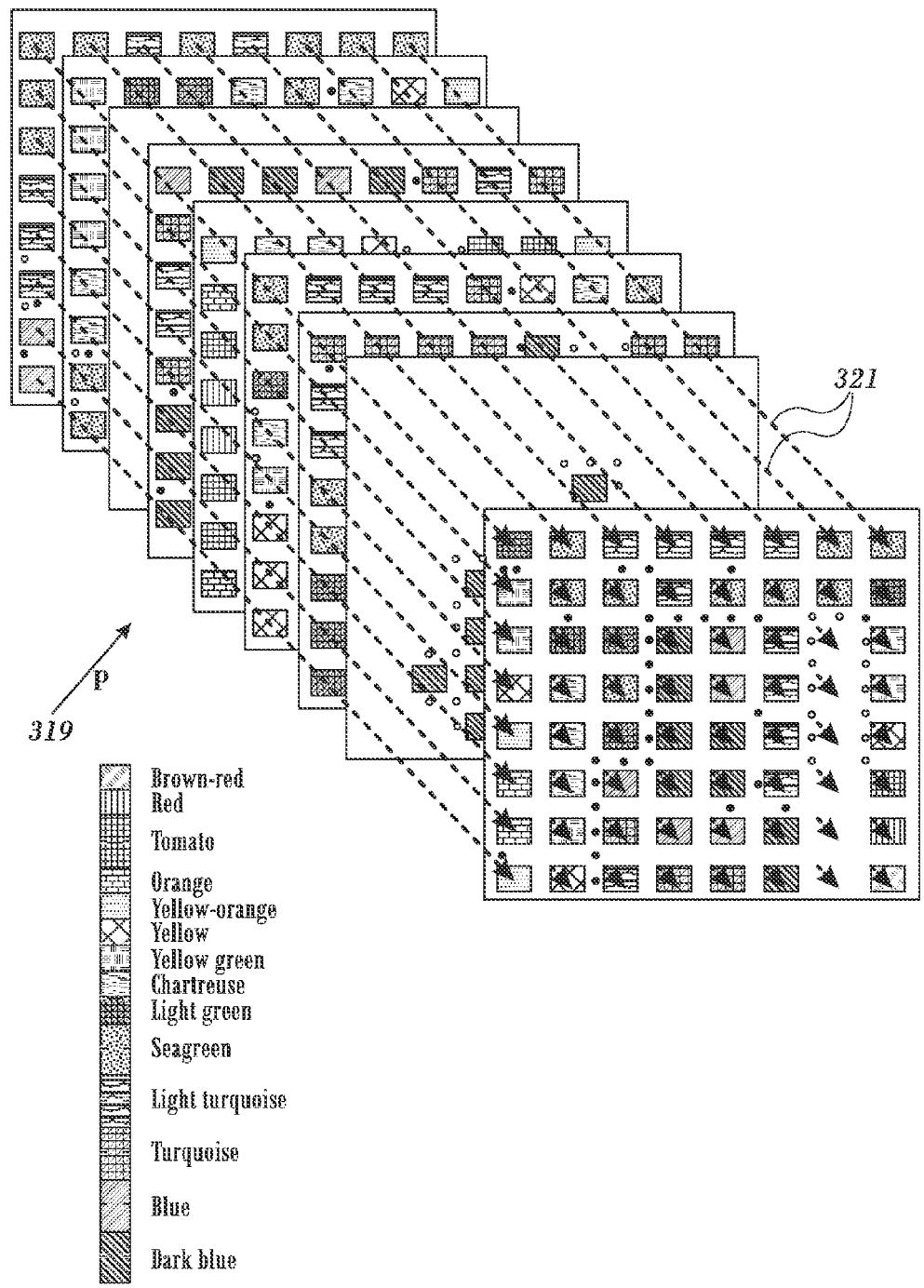
FIG. 34 is a diagram illustrating temporal analysis of a block/line electrode grid in accordance with an embodiment of the invention.

Reference is now made to FIG. 34, which is a diagram illustrating temporal analysis of a block/line electrode grid 319 in accordance with an embodiment of the invention. Time progression is indicated by arrows 321. Evolution of electrical propagation is evaluated, generally after performing the filtering procedures described above, by comparing successive instances of the propagation. The grid 319 is useful for generating block density and block stability maps.

Figure 35:
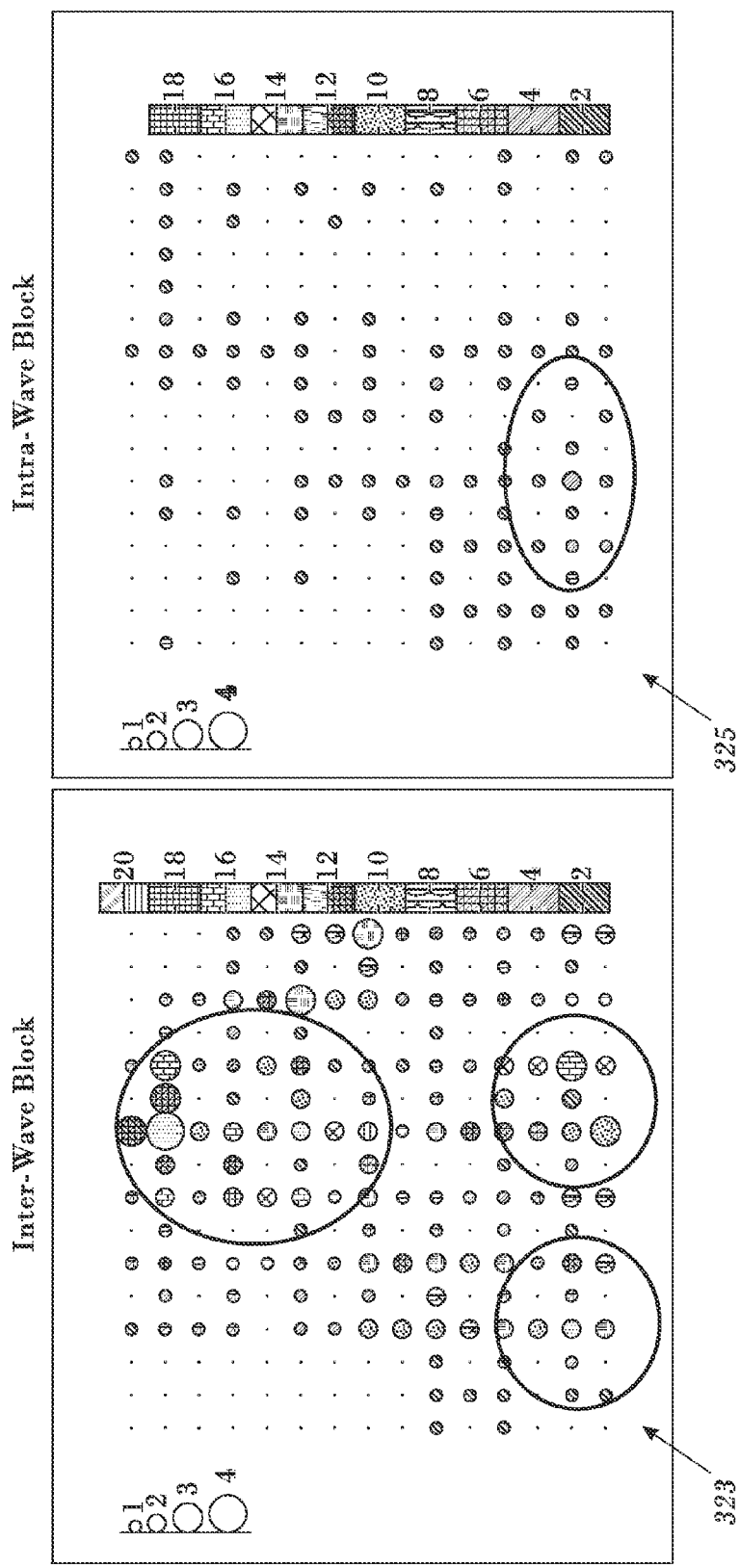
FIG. 35 is a set of diagrams of an electrode grid following temporal analysis in accordance with an embodiment of the invention.

Reference is now made to FIG. 35, which is a set of diagrams of an electrode grid following temporal analysis in accordance with an embodiment of the invention. Block-line filtering has been performed as described above. Circled areas in grid 323 indicate an interwave block. On grid 325 at the right of the figure an intrawave block is circled. The grids represent an analysis of 50 consecutive waves.

Simulator

According to an embodiment of the invention, the procedures described above are performed using a wave mapping simulator. This is useful to optimize the above-noted parameters of operation. A tool developed for this purpose accepts as input a mapping array of electrode locations in two or three dimensions. The electrode locations are specified in the x, y, and z direction. Annotation times are expressed in terms of conduction velocity vectors.

The simulator generates planar waves in various angles with respect to the mapping array, and dissociated waves with block lines. Wave fusion and collision are simulated as well. The framework extendible to include breakthroughs and rotors and LAT windows.

Figure 36:
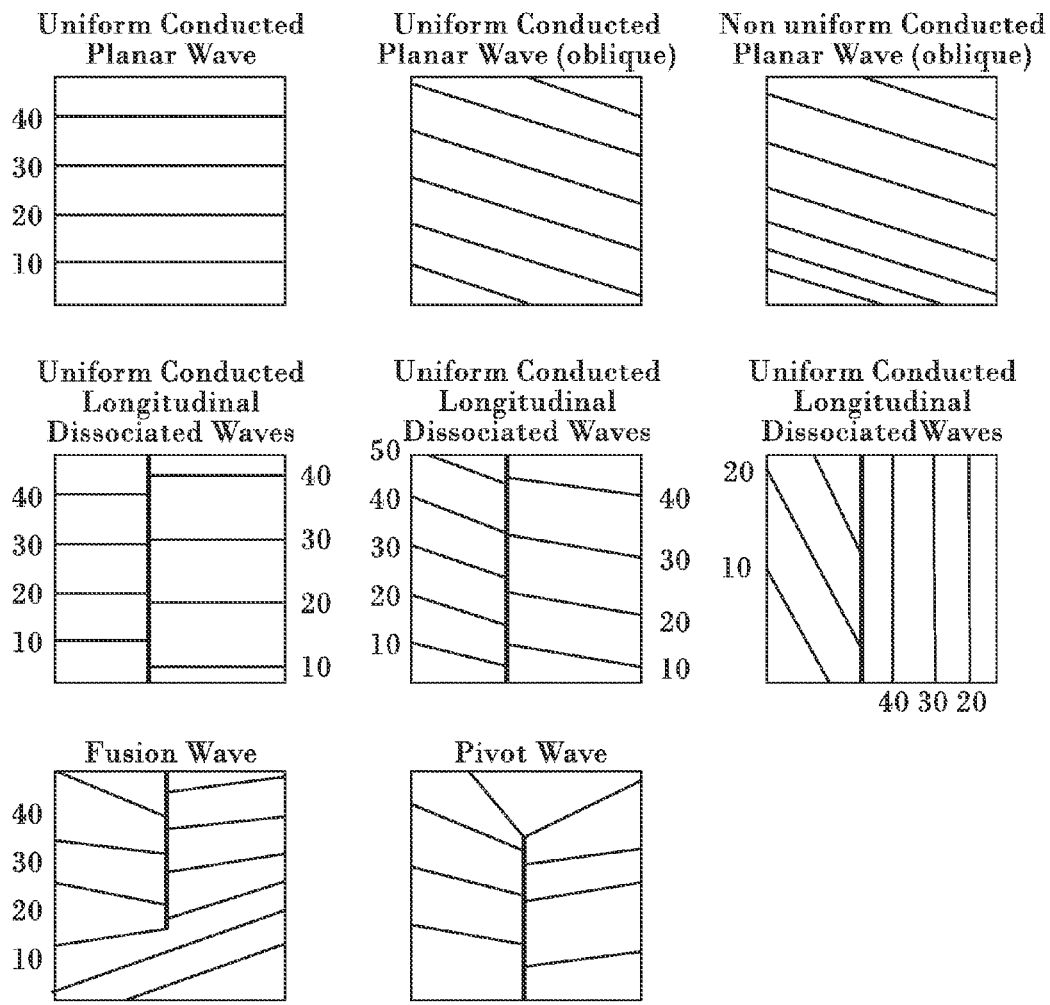
FIG. 36 is a series of diagrams illustrating wave activation configurations produced by a simulator in accordance with an embodiment of the invention.

Reference is now made to FIG. 36, which is a series of diagrams illustrating wave activation configurations produced by a simulator in accordance with an embodiment of the invention. These configurations may be processed by the previous embodiment to identify lines of block as described above.

Figure 37:
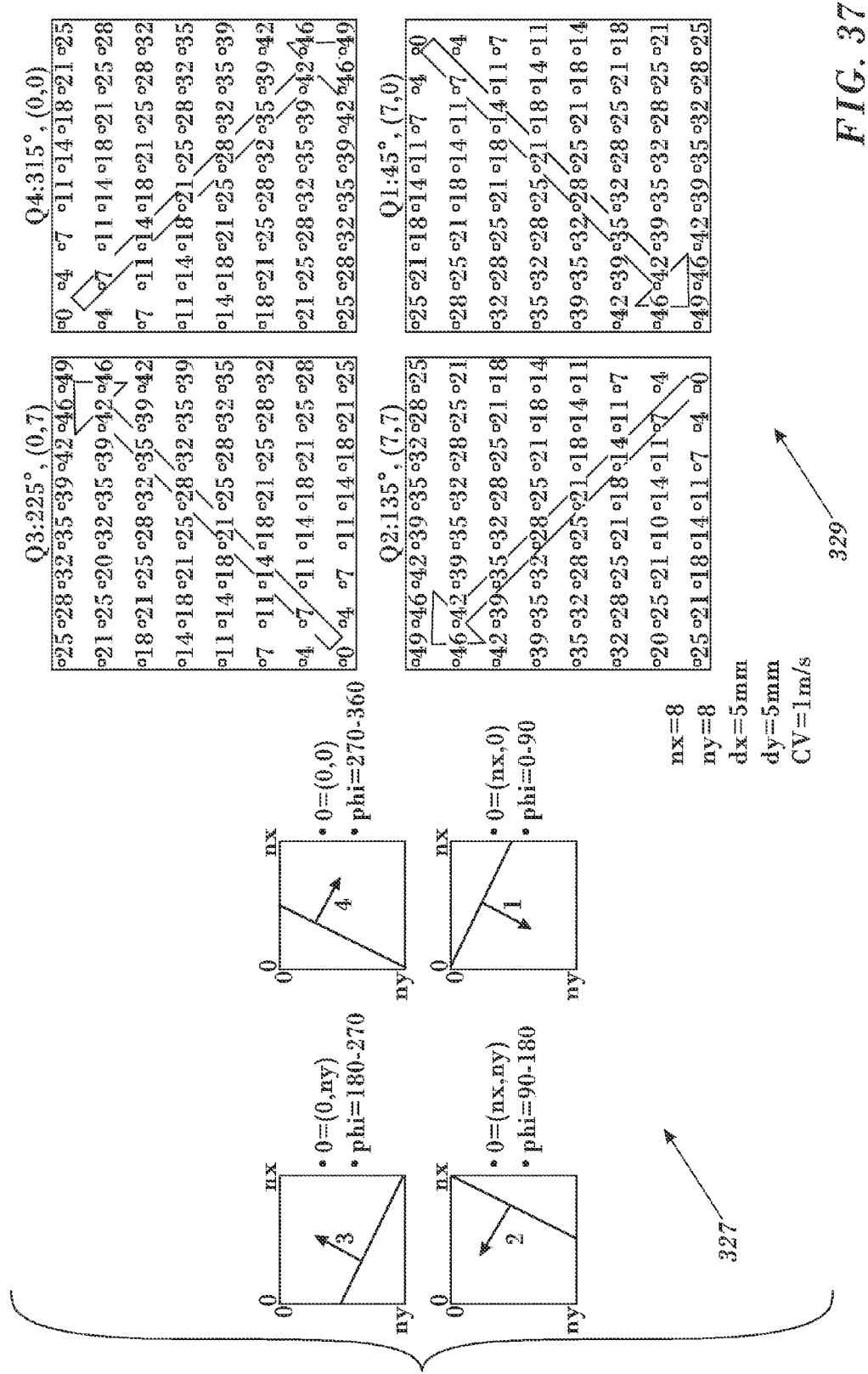
FIG. 37 is a series of conduction velocity vectors developed from wave fronts by a simulator in accordance with an embodiment of the invention.

Reference is now made to FIG. 37, which is a series of conduction velocity vectors developed from wave fronts by a simulator, in accordance with an embodiment of the invention. The values nx, ny refer to the number of electrodes in the x- and y-directions, respectively. The wave fronts are shown in a group 327 at the left of the figure. The conduction velocity vectors superimposed on corresponding grids of electrodes is presented in a group 329 at the right of the figure.

Figure 38:
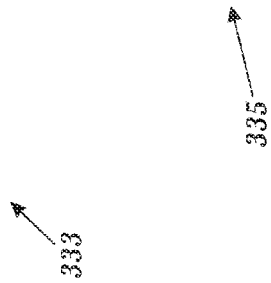
FIG. 38 is a composite diagram showing a simulated planar conduction velocity vector and wave front activation maps in accordance with an embodiment of the invention.

Reference is now made to FIG. 38, which is a composite diagram showing a simulated planar conduction velocity vector 331, which is parallel to the y-direction of the electrode array superimposed on a grid of electrodes 333 and corresponding wave front activation maps 335 in accordance with an embodiment of the invention.

Reference is now made to FIG. 39, which is a composite diagram showing the simulated planar parallel conduction velocity vector 331 (FIG. 38) superimposed on the grid of electrodes 333 together with corresponding activation maps 337, in accordance with an embodiment of the invention.

Reference is now made to FIG. 40, which is a composite diagram showing a graph 339 illustrating LAT jitter added to the simulated conduction velocity vector 331 (FIG. 38) and the effect of the jitter on activation maps 341, in accordance with an embodiment of the invention. A number of spurious blocks, some of which are indicated by dots 343, have appeared on the activation maps 341.

Reference is now made to FIG. 41, which is a composite diagram showing a simulated planar dissociated wave pattern in accordance with an embodiment of the invention. An 8×8 grid is shown. Two waves appear at LATs indicated in the upper part of the figure, with conduction velocity vectors 345, 347. Iterative progression of the waves is seen on the lower portion of the figure.

Figure 42:
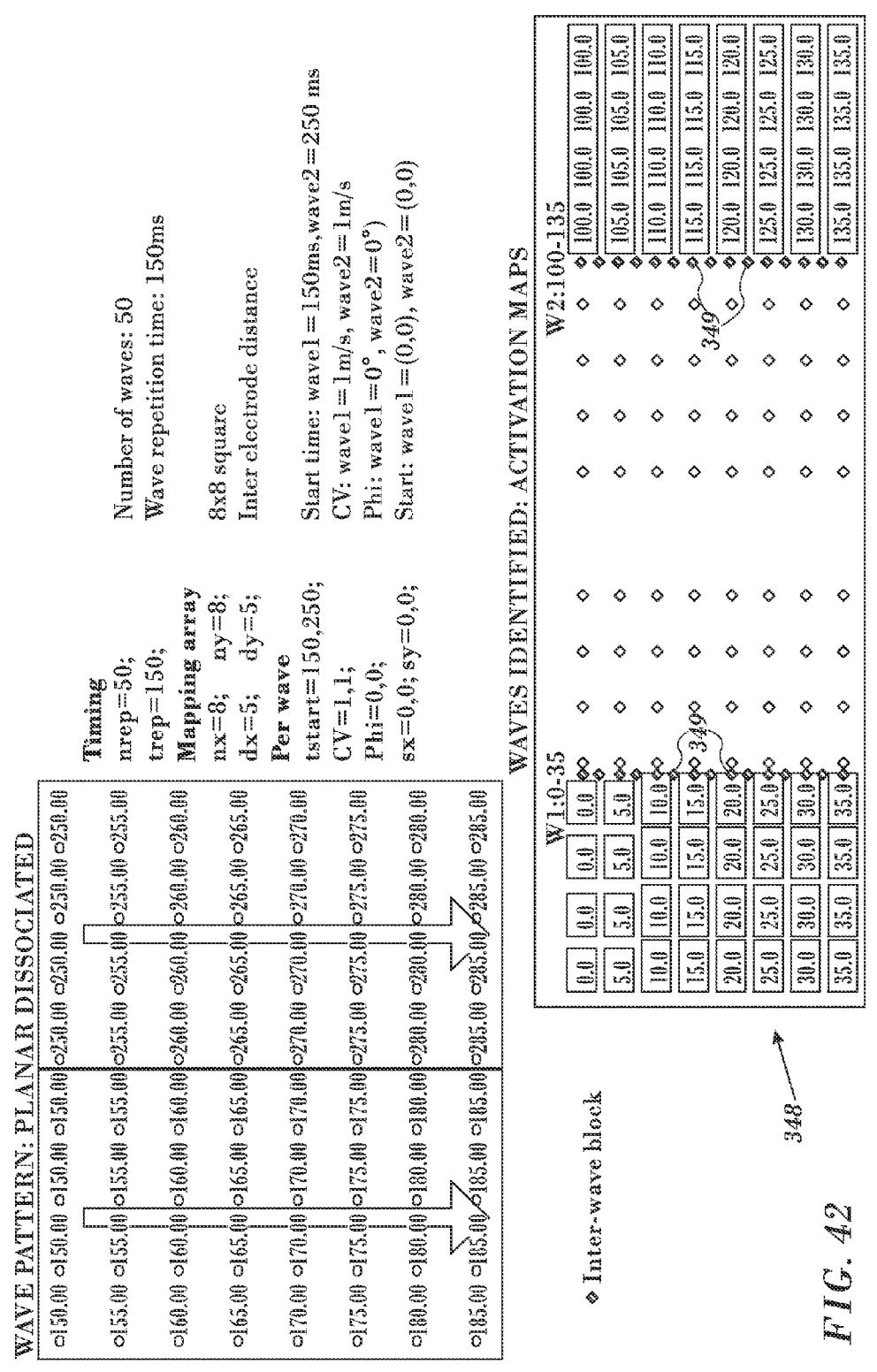

Reference is now made to FIG. 42, which is a composite diagram showing activation maps 348 of the planar dissociated wave pattern of FIG. 41 in accordance with an embodiment of the invention. A wave block is denoted by rows 349 of dots.

Figure 43:
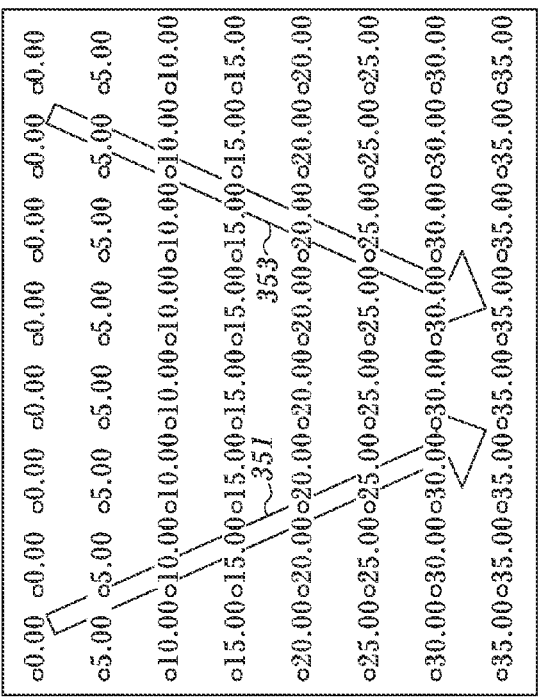
FIG. 43 is a composite diagram showing a simulated planar fusion wave pattern, in accordance with an embodiment of the invention.

Reference is now made to FIG. 43, which is a composite diagram showing a simulated planar fusion wave pattern, in accordance with an embodiment of the invention. The format is the same as FIG. 41, except now conduction velocity vectors 351, 353 converge. Corresponding activation maps 355 are shown in the lower portion of the figure.

Reference is now made to FIG. 44, which is a composite diagram showing a simulated planar reversal (u-turn) pattern in accordance with an embodiment of the invention. The format is the same as FIG. 41. Reversal of conduction velocity vectors 357, 359, 361 is shown. Corresponding activation maps 363 are shown in the lower portion of the figure.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
inserting a probe into a heart of a living subject, the probe having a plurality of electrodes;
recording electrograms from the electrodes at respective locations in the heart;
determining slopes and annotations in the electrograms within time windows;
establishing relationships among the slopes and annotations from different ones of the electrograms; and
determining from the relationships lines of conduction block in the heart;
wherein determining slopes and annotations comprises the steps of:
determining bipolar windows in the electrograms;
annotating local activation times within the bipolar windows;
determining from readings of a set of electrodes that a block point exists in a region of the set of electrodes;
repositioning the local activation times responsively to the block point; and
determining revised windows that include respective local activation times; and
wherein establishing relationships among the slopes and annotations comprises:
identifying primary slopes and secondary slopes in the electrograms;

determining whether the electrodes are in contact with the heart; and determining whether the primary slopes and the secondary slopes are coupled to one another.

2. The method according to claim 1, further comprising the step of generating an electroanatomic map of the lines of conduction block.

3. The method according to claim 1, further comprising the step of identifying a propagation wave responsively to determining whether the primary slopes and the secondary slopes are coupled to one another and determining whether the electrodes are in contact with the heart.

4. The method according to claim 1, further comprising the steps of:

computing conduction velocity vectors at the electrodes from the electrograms;

making a determination that an activation at a first electrode is dissociated from an activation at a second electrode; and concluding responsively to the determination that a conduction block exists between the first electrode and the second electrode.

5. The method according to claim 1, further comprising segmenting the electrograms into frames at respective times, wherein the frames are respective assignments of individual readings of a mesh of electrode readings to a matrix of values.

6. The method according to claim 5, wherein the frames comprise vacant positions that are unassigned to readings of the electrodes.

7. The method according to claim 5, wherein the frames comprise vacant positions, further comprising reassigning readings of the electrodes that are identified with an inter-wave block to the vacant positions.

8. The method according to claim 5, further comprising generating electroanatomic maps of the heart from the frames.

9. An apparatus, comprising:

a probe having a plurality of electrodes and adapted for insertion into a heart of a living subject; and a processor, which is configured to receive an electrical signal from the electrodes and to perform the steps of:

recording electrograms from the electrodes at respective locations in the heart;

determining slopes and annotations in the electrograms within time windows;

establishing relationships among the slopes and annotations from different ones of the electrograms; and determining from the relationships lines of conduction block in the heart;

wherein determining slopes and annotations comprises the steps of:

determining bipolar windows in the electrograms;

annotating local activation times within the bipolar windows;

determining from readings of a set of electrodes that a block point exists in a region of the set of electrodes;

repositioning the local activation times responsively to the block point; and determining revised windows that include respective local activation times; and wherein establishing relationships among the slopes and annotations comprises:

identifying primary slopes and secondary slopes in the electrograms;

determining whether the electrodes are in contact with the heart; and determining whether the primary slopes and the secondary slopes are coupled to one another.

10. The apparatus according to claim 9, further comprising a display, wherein the processor is further configured for generating an electroanatomic map of the lines of conduction block on the display.

11. The apparatus according to claim 9, wherein the processor is further configured for identifying a propagation wave responsively to determining whether the primary slopes and the secondary slopes are coupled to one another and determining whether the electrodes are in contact with the heart.

12. The apparatus according to claim 9, wherein the processor is further configured for:

computing conduction velocity vectors at the electrodes from the electrograms;

making a determination that an activation at a first electrode is dissociated from an activation at a second electrode; and concluding responsively to the determination that a conduction block exists between the first electrode and the second electrode.

13. The apparatus according to claim 9, wherein the processor is further configured for segmenting the electrograms into frames at respective times, wherein the frames are respective assignments of individual readings of a mesh of electrode readings to a matrix of values.

14. The apparatus according to claim 13, wherein the frames comprise vacant positions that are unassigned to readings of the electrodes.

15. The apparatus according to claim 13, wherein the frames comprise vacant positions, further comprising reassigning readings of the electrodes that are identified with an inter-wave block to the vacant positions.

16. The apparatus according to claim 13, wherein the processor is further configured for generating electroanatomic maps of the heart from the frames.

* * * * *